(12) United States Patent
Tryggvason et al.

(10) Patent No.: US 9,534,038 B2
(45) Date of Patent: Jan. 3, 2017

(54) ISOLATED LAMININ-421

(75) Inventors: Karl Tryggvason, Djursholm (SE); Sergey Rodin, Stockholm (SE)

(73) Assignee: BIOLAMINA AB, Stockholm (SE)

( * ) Notice: Subject to any disclaimer, the term of this patent is extended or adjusted under 35 U.S.C. 154(b) by 0 days.

(21) Appl. No.: 13/409,594

(22) Filed: Mar. 1, 2012

(65) Prior Publication Data

US 2012/0302512 A1  Nov. 29, 2012

Related U.S. Application Data

(60) Provisional application No. 61/447,818, filed on Mar. 1, 2011.

(51) Int. Cl.
*C12N 15/12* (2006.01)
*A61K 38/39* (2006.01)
*C07K 14/78* (2006.01)
*A61K 38/00* (2006.01)

(52) U.S. Cl.
CPC .............. *C07K 14/78* (2013.01); *A61K 38/00* (2013.01); *C07K 2319/033* (2013.01); *C07K 2319/036* (2013.01); *C07K 2319/09* (2013.01); *C07K 2319/41* (2013.01); *C07K 2319/43* (2013.01)

(58) Field of Classification Search
None
See application file for complete search history.

(56) References Cited

U.S. PATENT DOCUMENTS 6,638,907 B1 * 10/2003 Kortesmaa et al. ....... 424/185.1

FOREIGN PATENT DOCUMENTS

WO  WO 00/66732 A2  11/2000
WO  WO 02/50111 A2   6/2002

OTHER PUBLICATIONS

UniProtKB/Swiss-Pro Primary Accession No. Q16363 at http://www.uniprot.org/uniprot/Q16363, accessed Nov. 7, 2012.*
UniProtKB/Swiss-Pro Primary Accession No. P55268 at http://www.uniprot.org/uniprot/P55268, accessed Nov. 7, 2012.*

International Search Report and Written Opinion for International Application No. PCT/IB2012/000519, International Filing Date Mar. 1, 2012 mailed Jul. 4, 2012, 15 pages.
Saito Noriko et al: "Laminin-421 produced by lymphatic endothelial cells induces chemotaxis for human melanoma cells", Pigment Cell & Melanoma Research, vol. 22, No. 5, Oct. 2009 (Oct. 2009), pp. 601-610, XP002678239.
Miner J et al: "The laminin alpha chains: expression, developmental transitions, and chromosomal locations of alpha1-5, identification of heterotrimeric laminins 8-11, and cloning of a novel alpha3 isoform", The Journal of Cell Biology, Rockefeller University Press, US, vol. 137, No. 3, May 5, 1997 (May 5, 1997), pp. 685-701, XP002155046.
Kortesmaa J et al: "Recombinant laminin-8 (alpha(4)beta(1)gamma(1)). Production, purification, and interactions with integrins", Journal of Biological Chemistry, The American Society of Biological Chemists, Inc., US, vol. 275, No. 20, May 19, 2000 (May 19, 2000), pp. 14853-14859, XP002155048.
Aumailley M et al: "A simplified laminin nomenclature", Matrix Biology, Elsevier, NL, vol. 24, No. 5, Aug. 1, 2005 (Aug. 1, 2005), pp. 326-332, XP027787658.
Wewer U M et al: "Human beta2 Chain of Laminin (Formerly S Chain): cDNA Cloning, Chromosomal Localization, and Expression in Carcinomas", Genomics, Academic Press, San Diego, US, vol. 24, No. 2, Nov. 15, 1994 (Nov. 15, 1994), pp. 243-252, XP024796069.
Iivanainen A et al: "The Human Laminin Beta2 Chain (S-Laminin): Structure, Expression Infetal Tissues and Chromosomal Assignment of the Lamb2 Gene", Matrix Biology, XX, XX, vol. 14, No. 6, Jan. 1, 1994 (Jan. 1, 1994), pp. 489-497, XP001018137.
Richards A et al: "The Complete CDNA Sequence of Laminin Alpha4 and Its Relationship to the Other Human Laminin Alpha Chains", European Journal of Biochemistry, Blackwell Publishing, Berlin, DE, vol. 238, No. 3, Jun. 15, 1996 (Jun. 15, 1996), pp. 813-821, XP000942244.
Wondimu Z et al: "Characterization of commercial laminin preparations from human placenta in comparison to recombinant laminins 2 (alpha2beta1gamma1), 8 (alpha4beta1gamma1), 10 (alpha5beta1gamma1)", Matrix Biology, Elsevier, NL, vol. 25, No. 2, Mar. 1, 2006 (Mar. 1, 2006), pp. 89-93, XP027933611.

* cited by examiner

*Primary Examiner* — Julie Ha
*Assistant Examiner* — Kristina M Hellman
(74) *Attorney, Agent, or Firm* — Richard M. Klein; Fay Sharpe LLP

(57) ABSTRACT

The present disclosure provides isolated laminin-421, methods for making recombinant laminin-421, and host cells that express recombinant laminin-421. The present disclosure also provides nucleic acid sequences encoding full length human laminin β2 chain, expression vectors and host cells thereof.

4 Claims, No Drawings

ISOLATED LAMININ-421

This application claims priority to U.S. Provisional Patent Application Ser. No. 61/447,818, filed on Mar. 1, 2011, the entirety of which is hereby fully incorporated by disclosure herein.

BACKGROUND

This application relates to cell biology, cell differentiation, cell therapy, molecular biology, proteins, nucleic acids, and laminins.

Basal laminae (basement membranes) are sheet-like, cell-associated extracellular matrices that play a central role in cell growth, cellular differentiation, cell phenotype maintenance, tissue development, and tissue maintenance. They are present in virtually all tissues, and appear in the earliest stages of embryonic development.

Basal laminae are central to a variety of architectural and cell-interactive functions. For example:

1. They serve as architectural supports for tissues, providing adhesive substrata for cells.

2. They create perm-selective barriers between tissue compartments that impede the migration of cells and passively regulate the exchange of macromolecules. These properties are illustrated by the kidney glomerular basement membrane, which functions as an important filtration structure, creating an effective blood-tissue barrier that is not permeable to most proteins and cells.

3. Basal laminae create highly interactive surfaces that can promote cell migration and cell elongation during embryogenesis and wound repair. Following an injury, they provide a surface upon which cells regenerate to restore normal tissue function.

4. Basal laminae present information encoded in their structure to contacting cells that is important for cellular differentiation, prevention of apoptosis, and tissue maintenance. This information is communicated to the cells through various receptors that include the integrins, dystroglycan, and cell surface proteoglycans. Signaling is dependent not only on the presence of matrix ligands and corresponding receptors that interact with sufficient affinities, but also on such topographical factors as ligand density in a three-dimensional matrix "landscape", and on the ability of basal lamina components to cluster receptors. Because these matrix proteins can be long-lived, basal laminae create a "surface memory" in the basal lamina for resident and transient cells.

The basal lamina is largely composed of laminin and type IV collagen heterotrimers that in turn become organized into complex polymeric structures. To date, six types IV collagen polypeptide chains and at least twelve laminin subunit chains have been identified. These chains possess shared and unique functions and are expressed with specific temporal (developmental) and spatial (tissue-site specific) patterns.

Laminins are a family of heterotrimeric glycoproteins that reside primarily in the basal lamina. They function via binding interactions with neighboring cell receptors on the one side, and by binding to other laminin molecules or other matrix proteins such as collagens, nidogens or proteoglycans. The laminin molecules are also important signaling molecules that can strongly influence cellular function. Laminins are important in both maintaining cell/tissue phenotype as well as promoting cell growth and differentiation in tissue repair and development.

Laminins are large, multi-domain proteins, with a common structural organization. The laminin molecule integrates various matrix and cell interactive functions into one molecule.

A laminin molecule is comprised of one α-chain subunit, one β-chain subunit, and one γ-chain subunit, all joined together through a coiled-coil domain. The twelve laminin subunit chains can form at least 15 trimeric laminin types in native tissues. Within the trimeric laminin structures are identifiable domains that possess binding activity towards other laminin and basal lamina molecules, and membrane-bound receptors. Domains VI, IVb, and IVa form globular structures, and domains V, IIIb, and IIIa (which contain cysteine-rich EGF-like elements) form rod-like structures. Domains I and II of the three chains participate in the formation of a triple-stranded coiled-coil structure (the long arm).

Four structurally-defined family groups of laminins have been identified. The first group of five identified laminin molecules all share the β1 and γ1 chains, and vary by their α-chain composition (α1 to α5 chain). The second group of five identified laminin molecules, including laminin-421, all share the β2 and γ1 chain, and again vary by their α-chain composition. The third group of identified laminin molecules has one identified member, laminin-332, with a chain composition of α3β3γ2. The fourth group of identified laminin molecules has one identified member, laminin-213, with the newly identified γ3 chain (α2β1γ3).

There have been no reports of isolated laminin-421 that is free of other laminin chains. Thus far, there are no studies on the function of laminin-421. Attempts to purify laminin-421 from cell sources by affinity chromatography using laminin chain antibodies have been unsuccessful in eliminating, for example, laminin β1 chain, which is a component of laminin-411.

The function of laminin-421 would be important to study using purified molecules. The availability of pure laminin-421 would enable studies of the effects of the protein on cellular differentiation and maintenance of cellular phenotypes. Thus, numerous research and therapeutic purposes including, but not limited to, treating injuries to tissues, promoting cell attachment, expansion and migration, ex vivo cell therapy, improving the biocompatibility of medical devices, and preparing improved cell culture devices and media, would be furthered if pure laminin-421 were available.

Thus, there is a need in the art for isolated laminin-421 for research and therapeutic purposes, and methods for making isolated laminin-421.

BRIEF DESCRIPTION

The present disclosure provides isolated laminin-421 and methods for producing isolated laminin-421. In further aspects, the present disclosure provides recombinant host cells that express laminin-421 chains and secrete recombinant laminin-421.

In other aspect, the present disclosure provides GMP quality laminin-421 for culturing cells for differentiation and maintenance for the purpose of developing cells for human cell therapy. The present disclosure also provides pharmaceutical compositions, comprising isolated laminin-421 together with a pharmaceutically acceptable carrier. Such pharmaceutical compositions can optionally be provided with other extracellular matrix components.

The present disclosure also provides methods to effectively generate amounts of isolated laminin-421 for various uses. In preferred embodiments of those uses, recombinant laminin-421 is used. Kits comprising an amount of isolated laminin-421, or pharmaceutical compositions thereof, effective for the desired effect, and instructions for the use thereof, are also disclosed.

In further aspects, the present disclosure provides improved medical devices and grafts, wherein the improvement comprises providing medical devices and grafts with an effective amount of isolated laminin-421, or a pharmaceutical composition of the present disclosure.

In further aspects, the disclosure provides improved cell culture devices, and methods for preparing improved cell culture devices, for the growth and maintenance of phenotypes of cells in culture, by providing an effective amount of isolated laminin-421 to a cell culture device for cell attachment, and subsequent cell stasis, proliferation, differentiation, and/or migration.

These and other non-limiting characteristics of the disclosure are more particularly disclosed below.

DETAILED DESCRIPTION

A more complete understanding of the compositions and methods disclosed herein can be obtained by reference to the following description. The specific details of the description are not intended to define or limit the scope of the exemplary embodiments.

Although specific terms are used in the following description for the sake of clarity, these terms are intended to refer only to the particular structure of the embodiments described herein, and are not intended to define or limit the scope of the disclosure.

All references, patents and patent applications discussed herein are hereby incorporated by reference in their entirety.

Within this application, unless otherwise stated, the techniques utilized may be found in any of several well-known references such as: Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2.sup.nd Ed. (R. I. Freshney. 1987. Liss, Inc. New York, N.Y.), Gene Transfer and Expression Protocols, pp. 109-128, ed. E. J. Murray, The Humana Press Inc., Clifton, N.J.), and the Ambion 1998 Catalog (Ambion, Austin, Tex.).

An used herein, an "isolated nucleic acid sequence" refers to a nucleic acid sequence that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). An "isolated" laminin β2 chain nucleic acid sequence according to the present disclosure may, however, be linked to other nucleotide sequences that do not normally flank the recited sequence, such as a heterologous promoter sequence, or other vector sequences. It is not necessary for the isolated nucleic acid sequence to be free of other cellular material to be considered "isolated", as a nucleic acid sequence according to the disclosure may be part of an expression vector that is used to transfect host cells (see below).

The present disclosure provides recombinant expression vectors comprising a full length laminin β2 chain nucleic acid sequence (SEQ ID NO: 4) of the human laminin β2 chain. In some embodiments, the expression vectors comprise a nucleic acid encoded by SEQ ID NO: 4, operatively linked to a heterologous promoter (i.e. is not the naturally occurring promoter for the given β2 laminin chain). A promoter and a laminin β2 chain nucleic acid sequence are "operatively linked" when the promoter is capable of driving expression of the laminin β2 chain DNA into RNA.

As used herein, the term "vector" refers to a nucleic acid molecule capable of transporting another nucleic acid to which it has been linked. One type of vector is a "plasmid", which refers to a circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors), are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In the present disclosure, the expression of the laminin polypeptide sequence is directed by the promoter sequences of the disclosure, by operatively linking the promoter sequences of the disclosure to the gene to be expressed. In general, expression vectors of utility in recombinant DNA techniques are often in the form of plasmids. In the present specification, "plasmid" and "vector" may be used interchangeably, as the plasmid is the most commonly used form of vector. However, the disclosure is intended to include other forms of expression vectors, such as viral vectors (e.g., replication defective retroviruses, adenoviruses and adeno-associated viruses), which serve equivalent functions.

The vector may also contain additional sequences, such as a polylinker for subcloning of additional nucleic acid sequences, or a polyadenylation signal to effect proper polyadenylation of the transcript. The nature of the polyadenylation signal is not believed to be crucial to the successful practice of the methods of the disclosure, and any such sequence may be employed, including but not limited to the SV40 and bovine growth hormone poly-A sites. Also contemplated as an element of the vector is a termination sequence, which can serve to enhance message levels and to minimize read through from the construct into other sequences. Additionally, expression vectors typically have selectable markers, often in the form of antibiotic resistance genes, that permit selection of cells that carry these vectors.

In further embodiments, the present disclosure provides host cells transfected with the laminin β2 chain-expressing recombinant expression vectors disclosed herein. As used herein, the term "host cell" is intended to refer to a cell into which a nucleic acid of the present disclosure, such as a recombinant expression vector, has been introduced. Such cells may be prokaryotic, which can be used, for example, to rapidly produce a large amount of the expression vectors of the disclosure, or may be eukaryotic, for functional studies.

The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The host cells can be transiently or stably transfected with one or more of the expression vectors of the disclosure. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2.sup.nd Ed. (R. I. Freshney. 1987. Liss, Inc. New York, N.Y.).

In another aspect, the present disclosure provides an isolated full length human laminin β2 chain polypeptide consisting of the amino acid sequence of SEQ ID NO: 2.

As used herein, an "isolated polypeptide" refers to a polypeptide that is substantially free of other proteins, including other laminin chains, and gel agents, such as polyacrylamide and agarose. In preferred embodiments, the isolated laminin polypeptide is free of detectable contaminating laminin chains. Thus, the protein can either be isolated from natural sources, or recombinant protein can be isolated from the transfected host cells disclosed above.

In another aspect, the present disclosure provides isolated laminin-421. As used herein "laminin-421" encompasses both recombinant laminin-421 and heterotrimeric laminin-421 from naturally occurring sources. In preferred embodiments, the laminin-421 comprises recombinant laminin-421 (or "r-laminin-421").

As used herein, the term "r-laminin-421" refers to recombinant heterotrimeric laminin-421, expressed by a host cell that has been transfected with one or more expression vectors comprising at least one nucleic acid sequence encoding a laminin-421 chain selected from the α4, β2 and γ1 chains, or processed/secreted forms thereof. Such r-laminin-421 can thus comprise α4, β2, and γ1 sequences from a single organism, or from different organisms. Various laminin-421 chain DNA sequences are known in the art, and the use of each to prepare the r-laminin-421 of the disclosure is contemplated. (See, for example, Pouliot, N. et al., Experimental Cell Research 261(2):360-71, (2000); Kikkawa, Y. et al., Journal of Cell Science 113 (Pt 5):869-76, (2000); Church, H J. et al., Biochemical Journal 332 (Pt 2):491-8, (1998); Sorokin, L M. et al., Developmental Biology 189 (2):285-300, (1997); Miner, J H. et al., Journal of Biological Chemistry 270(48):28523-6, (1995); Sorokin, L. et al., European Journal of Biochemistry 223(2):603-10, (1994); all references being incorporated by reference herein in their entirety). In preferred embodiments, the r-laminin-421 comprises recombinant human α4, β2, and γ1 polypeptide chains.

The disclosure encompasses those laminin molecules wherein only one or two chains that make up the recombinant heterotrimeric laminin-421 are encoded by endogenous laminin-421 chains. In preferred embodiments, each of the α4, β2, and γ1 polypeptide chains are expressed recombinantly.

Laminin-421 is a secreted protein, which is capable of being directed to the endoplasmic reticulum (ER), secretory vesicles, and the extracellular space as a result of a signal sequence. If the secreted protein is released into the extracellular space, the secreted protein can undergo extracellular processing to produce a "mature" protein. Such processing event can be variable, and thus may yield different versions of the final "mature protein". The isolated laminin-421 of the present disclosure includes heterotrimers comprising both the full length and any such processed laminin-421 polypeptide chains.

As used herein, a laminin-421 polypeptide chain refers to a polypeptide chain according to one or more of the following:

(a) a polypeptide chain that comprises a polypeptide structure selected from the group consisting of: R1-R2-R3, R1-R2-R3(e), R3, R3(e), R1-R3, R1-R3(e), R2-R3, and R2-R3(e), wherein R1 is an amino terminal methionine; R2 is a signal sequence that is capable of directing secretion of the polypeptide, wherein the signal sequence may be the natural signal sequence for the particular laminin chain, that of another secreted protein, or an artificial sequence; R3 is a secreted laminin chain selected from the group consisting of a α4 chain, a β2 chain, and a γ1 chain; and R3(e) is a secreted β4, β2, or γ1 laminin chain that further comprises an epitope tag (such as those described below), which can be placed at any position within the laminin chain amino acid sequence; or (b) a polypeptide chain that is encoded by a polynucleotide that hybridizes under high or low stringency conditions to the coding regions, or portions thereof, of one or more of the recombinant laminin-421 chain DNA sequences disclosed herein (SEQ ID NO: 4, SEQ ID NO: 5, SEQ ID NO: 6), or complementary sequences thereof; or (c) a polypeptide chain that has at least 70% identity to one or more of the disclosed laminin-421 polypeptide chain amino acid sequences (SEQ ID NO: 1, SEQ ID NO: 2, SEQ ID NO: 3), preferably at least 80% identity, and most preferably at least about 90% identity.

"Stringency of hybridization" is used herein to refer to washing conditions under which nucleic acid hybrids are stable. The disclosure also includes nucleic acids that hybridize under high stringency conditions (as defined herein) to all or a portion of the coding sequences of the laminin chain polynucleotides disclosed herein, or their complements. The hybridizing portion of the hybridizing nucleic acids is typically at least 50 nucleotides in length. As known to those of ordinary skill in the art, the stability of hybrids is reflected in the melting temperature ($T_M$) of the hybrids. $T_M$ decreases approximately 1-1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. As used herein, high stringency refers to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Also contemplated are laminin-421-encoding nucleic acid sequences that hybridize to the polynucleotides of the present disclosure at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO_4$; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

As used herein, "percent identity" of two amino acids or of two nucleic acids is determined using the algorithm of Karlin and Altschul (Proc. Natl. Acad. Sci. USA 87:2264.2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score 100, wordlength=12, to determine nucleotide sequences identity to the nucleic acid molecules of the disclosure. BLAST protein searches are performed with the XBLAST program, score=50, wordlength=3, to determine an amino acid sequence identity to a polypeptide of the disclosure. To obtain gapped alignments for comparison purposes, Gapped BLAST is utilized as described in Altschul et al. (Nucleic Acids. Res. 25:3389-3402, 1997). When utilizing BLAST and Gapped BLAST programs, the default parameters of the respective programs (e.g., XBLAST and NBLAST) are used.

Further embodiments of the present disclosure include polynucleotides encoding laminin-421 chain polypeptides having at least 70% identity, preferably at least 80% identity, and most preferably at least 90% identity to one or more of the polypeptide sequences contained in SEQ ID NO: 4, SEQ ID NO: 5, and SEQ ID NO: 6.

As used herein, "α4 polynucleotide" refers to polynucleotides encoding an laminin α4 chain. Such polynucleotides can be characterized by one or more of the following: (a) polynucleotides that encode polypeptides which share at least 70% identity, preferably 80% identity, and most preferably at least 90% identity with a sequence selected of SEQ ID NO: 5; (b) the α4 polynucleotides hybridize under low or high stringency conditions to the coding sequence of SEQ ID NO: 5 or complementary sequences thereof; or (c) the α4 polynucleotides encode a laminin α4 chain polypeptide with a general structure selected from the group consisting of R1-R2-R3, R1-R2-R3(e), R3, R3(e), R1-R3, R1-R3(e), R2-R3, and R2-R3(e), wherein R1 and R2 are as described above, and R3 and R3(e) are as described above but comprise secreted α4 chain polypeptides.

As used herein, "β2 polynucleotides" refers to polynucleotides encoding a β2 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 4; (b) the β2 polynucleotides hybridize under low or high stringency conditions to the coding sequences of SEQ ID NO: 4, or complementary sequences thereof; or (c) the β2 polynucleotides encode a polypeptide with a general structure selected from R1-R2-R3, R1-R2-R3(e), R3, R3(e), R1-R3, R1-R3(e), R2-R3, and R2-R3(e), wherein R1 and R2 are as described above, and R3 and R3(e) are as described above but comprise secreted β2 chain polypeptides.

As used herein, "γ1 polynucleotides" refers to polynucleotides encoding a γ1 laminin chain of the same name. Such polynucleotides can be characterized by one or more of the following: (a) polynucleotides that encode polypeptides which share at least 70% identity, preferably at least 80%, and most preferably at least 90% identity with the sequence of SEQ ID NO: 6; (b) the γ1 polynucleotides hybridize under low or high stringency conditions to the coding sequence of SEQ ID NO: 6 or complementary sequences thereof; or (c) the γ1 polynucleotides encode a polypeptide with a general structure selected from R1-R2-R3, R1-R2-R3(e), R3, R3(e), R1-R3, R1-R3(e), R2-R3, and R2-R3(e), wherein R1 and R2 are as described above, and R3 and R3(e) are as described above but comprise secreted γ1 chain polypeptides.

As used herein, the term "epitope tag" refers to a polypeptide sequence that is expressed as part of a chimeric protein, where the epitope tag serves as a recognition site for binding of antibodies generated against the epitope tag, or for binding of other molecules that can be used for affinity purification of sequences containing the tag.

In preferred embodiments, cDNAs encoding the laminin α4, β2 and γ1 chains, or fragments thereof, are subcloned into an expression vector. Alternatively, laminin α4, β2 and/or γ1 gene sequences, including one or more introns, can be used for subcloning into an expression vector.

In other aspects, the present disclosure provides laminin-421 expressing-cells that have been transfected with an expression vector containing promoter sequences that are operatively linked to nucleic acid sequences encoding at least one polypeptide sequence comprising a sequence selected from the group consisting of the α4, β2 and γ1 chains of laminin-421, wherein the transfected cells secrete heterotrimeric laminin-421 containing the recombinant laminin chain. In preferred embodiments, the cells are systematically transfected with recombinant expression vectors containing promoter sequences that are operatively linked to nucleic acid sequences encoding polypeptide sequences comprising the α4, β2 and γ1 chains of laminin-421, which are even more preferably all human chains. After the multiple transfections, the cells express recombinant laminin-421 chains, which form the heterotrimeric r-laminin-421.

Transfection of the expression vectors into eukaryotic cells can be accomplished via any technique known in the art, including but not limited to calcium phosphate co-precipitation, electroporation, or liposome mediated-, DEAE dextran mediated-, polycationic mediated-, or viral mediated transfection. Transfection of bacterial cells can be done by standard methods.

In preferred embodiments, the cells are stably transfected. Methods for stable transfection and selection of appropriate transfected cells are known in the art. In other preferred embodiments, a CMV promoter driven expression vector is used in a human kidney embryonic 293 cell line.

Any cell capable of expressing and secreting the r-laminin-421 can be used. Preferably, eukaryotic cells are used, and most preferably mammalian cells are used, including but not limited to kidney and epithelial cell lines. The promoter sequence used to drive expression of the individual chains or r-laminin-421 may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). Carbohydrate and disulfide post-translational modifications are believed to be required for laminin-421 protein folding and function. This makes the use of eukaryotic cells preferable for producing functional r-laminin-421, although other systems are useful for obtaining, for example, antigens for antibody production. In most preferred embodiments, the mammalian cells do not express the laminin β2 chain endogenously. In other preferred embodiments, the cells do not express all of the laminin-421 chains endogenously.

The protein may comprise additional sequences useful for promoting purification of the protein, such as epitope tags and transport signals. Examples of such epitope tags include, but are not limited to FLAG (SIGMA CHEMICAL, St. Louis, Mo.), myc (9E10) (INVITROGEN, Carlsbad, Calif.), 6-His (INVITROGEN; NOVAGEN, Madison, Wis.), and HA (Boehringer Manheim Biochemicals). Examples of such transport signals include, but are not limited to, export signals, secretory signals, nuclear localization signals, and plasma membrane localization signals.

In some embodiments, at least one of the laminin chain polypeptide sequences, or fragments thereof, is operatively linked to a nucleic acid sequence encoding an "epitope tag", so that at least one of the chains is expressed as a fusion protein with an expressed epitope tag. The epitope tag may be expressed as the amino terminus, the carboxy terminus, or internal to any of the polypeptide chains comprising r-laminin-421, so long as the resulting r-laminin-421 remains functional.

In other embodiments, one of the r-laminin-421 chains is expressed as a fusion protein with a first epitope tag, and at least one other r-laminin chain is expressed as a fusion protein with a second epitope tag. This permits multiple rounds of purification to be carried out. Alternatively, the same epitope tag can be used to create fusion proteins with more than one of the r-laminin chains.

In further embodiments, the epitope tag can be engineered to be cleavable from the r-laminin-421 chain(s). Alternatively, no epitope tag is fused to any of the r-laminin-421 chains, and the r-laminin-421 is isolated by standard techniques, including but not limited to affinity chromatography using laminin-421 specific antibodies or other laminin-421 binding molecules.

Media from cells transfected with a single laminin chain are initially analyzed on Western blots using laminin chain-specific antibodies. The expression of single laminin chains following transfection is generally intracellular. Clones showing reactivity against individual transfected chain(s) are verified by any appropriate method, such as PCR, reverse transcription-PCR, or nucleic acid hybridization, to confirm incorporation of the transfected gene. Preferably, analysis of genomic DNA preparations from such clones is done by PCR using laminin chain-specific primer pairs. Media from transfected clones producing all three chains are further analyzed for r-laminin-421 secretion and/or activity, by any appropriate method, including Western blot analysis and cell binding assays.

In preferred embodiments, purification of r-laminin-421 is accomplished by passing media from the transfected cells through an antibody affinity column. In some embodiments, antibodies against a peptide epitope expressed on at least one of the recombinant chains are attached to an affinity column, and bind the r-laminin-421 that has been secreted into the media. The r-laminin-421 is removed from the column by passing excess peptide over the column. Eluted fractions are analyzed by any appropriate method, including gel electrophoresis and Western blot analysis. In further embodiments, the peptide epitope can be cleaved after purification. In other embodiments, two or three separate r-laminin chains are expressed as fusion proteins, each with a different epitope tag, permitting two or three rounds of purification and a doubly or triply isolated r-laminin-421. The epitope tag can be engineered so as to be cleavable from the r-laminin-421 chain(s) after purification. Alternatively, no epitope tag is fused to any of the r-laminin-421 chains, and the r-laminin-421 is isolated by standard techniques, including but not limited to affinity chromatography using laminin-421 specific antibodies or other laminin-421 binding molecules.

The laminin-421 polypeptide chains of the present disclosure also include (i) substitutions with one or more of the non-conserved amino acid residues, where the substituted amino acid residues may or may not be one encoded by the genetic code, or (ii) substitution with one or more amino acid residues having substituent groups, or (iii) fusion of the mature polypeptide with another compound, such as a compound to increase the stability and/or solubility of the polypeptide (for example, polyethylene glycol), or (iv) fusion of the polypeptide with additional amino acids, such as an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

In particular embodiments, the isolated laminin-421 comprises three chains. The first chain comprises a polypeptide with at least 80% identity to a polypeptide sequence of SEQ ID NO: 1 (i.e. the α4 laminin chain). The second chain comprises a polypeptide with at least 70% identity to a polypeptide sequence of SEQ ID NO: 2 (i.e. the β2 laminin chain). The third chain comprises a polypeptide with at least 70% identity to a polypeptide sequence of SEQ ID NO: 3 (i.e. the γ1 laminin chain). These first, second, and third chains are assembled into recombinant laminin-421.

In more specific embodiments, the polypeptide of the first chain has at least 80% identity to the polypeptide sequence of SEQ ID NO: 1, the polypeptide of the second chain has at least 80% identity to the polypeptide sequence of SEQ ID NO: 2, and the polypeptide of the third chain has at least 80% identity to the polypeptide sequence of SEQ ID NO: 3.

In more specific embodiments, the polypeptide of the first chain has at least 90% identity to the polypeptide sequence of SEQ ID NO: 1, the polypeptide of the second chain has at least 90% identity to the polypeptide sequence of SEQ ID NO: 2, and the polypeptide of the third chain has at least 90% identity to the polypeptide sequence of SEQ ID NO: 3.

In particular embodiments, the first chain comprises the polypeptide sequence of SEQ ID NO: 1, the second chain comprises the polypeptide sequence of SEQ ID NO: 2, and the third chain comprises the polypeptide sequence of SEQ ID NO: 3.

In particular embodiments, the first chain is the polypeptide sequence of SEQ ID NO: 1, the second chain is the polypeptide sequence of SEQ ID NO: 2, and the third chain is the polypeptide sequence of SEQ ID NO: 3.

The present disclosure further provides pharmaceutical compositions comprising isolated laminin-421 and a pharmaceutical acceptable carrier. In preferred embodiments, the pharmaceutical composition comprises isolated r-laminin-421. According to these aspects of the disclosure, other agents can be included in the pharmaceutical compositions, depending on the condition being treated. The pharmaceutical composition may further comprise one or more other compounds, including but not limited to any of the collagens, other laminin types, fibronectin, vitronectin, cadherins, integrins, α-dystroglycan, entactin/nidogen, α-dystroglycan, glycoproteins, proteoglycans, heparan sulfate proteoglycan, glycosaminoglycans, epidermal growth factor, vascular endothelial growth factor, fibroblast growth factor, or nerve growth factors, and peptide fragments thereof.

Pharmaceutical preparations comprising isolated laminin-421 can be prepared in any suitable form, and generally comprise the isolated laminin-421 in combination a pharmaceutically acceptable carrier. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifungals, antioxidants, osmotic agents, and similar materials in composition and quantity as is conventional. Suitable solutions for use in accordance with the disclosure are sterile, are not harmful for the proposed application, and may be subjected to conventional pharmaceutical operations such as sterilization and/or may contain conventional adjuvants, such as preservatives, stabilizers, wetting agents, emulsifiers, buffers etc. For assistance in formulating the compositions of the present disclosure, one may refer to Remington's Pharmaceutical Sciences, 15th Ed., Mack Publishing Co., Easton, Pa. (1975).

In further aspects, the present disclosure comprises medical devices with improved biocompatibility, wherein the devices are coated with isolated laminin-421 or pharmaceutical compositions thereof, alone or in combination with other proteins or agents that serve to increase the biocompatibility of the device surface. The coated device stimulates cell attachment (such as endothelial cell attachment), and provides for diminished inflammation and/or infection at the site of entry of the appliance.

Such medical devices can be of any material used for implantation into the body, and preferably are made of or coated with a biocompatible metal that may be either stainless steel or titanium. Alternatively, the device is made of or coated with a ceramic material, or a polymer including but not limited to polyester, polyglycolic acid or a polygalactose-polyglycolic acid copolymer.

If the device is made of a natural or synthetic biodegradable material in the form of a mesh, sheet or fabric, isolated laminin-421 or pharmaceutical compositions thereof may be applied directly to the surface thereof. Appropriate cells may then be cultured on the matrix to form transplantable or implantable devices, including dental abutment pieces, needles, metal pins or rods, indwelling catheters, colostomy tubes, surgical meshes and any other appliance for which coating with isolated laminin-421 is desirable. Alternatively, the devices may be implanted and cells may be permitted to attach in vivo.

Coupling of the isolated laminin-421 may be non-covalent (such as by adsorption), or by covalent means. The device may be immersed in, incubated in, or sprayed with the isolated laminin-421 or pharmaceutical compositions thereof.

The dosage regimen for various treatments using the isolated laminin-421 of the present disclosure is based on a variety of factors, including the type of injury or condition, the age, weight, sex, medical condition of the individual, the severity of the condition, and the route of administration. Thus, the dosage regimen may vary widely, but can be determined routinely by a physician using standard methods. Laminins are extremely potent molecules, and one or a few molecules per cell could produce an effect. Thus, effective doses in the pico-gram per milliliter range are possible if the delivery is optimized.

The following examples are for purposes of further illustrating the present disclosure. The examples are merely illustrative and are not intended to limit devices made in accordance with the disclosure to the materials, conditions, or process parameters set forth therein.

EXAMPLES

Cloning of the Human Laminin β2 cDNA

The 5.6 kb fragment of human laminin β2 cDNA was PCR-amplified from human liver cDNA library (BD Biosciences) using primers 5'-GTGGTACCCACAGGCA-GAGTTGAC-3' (SEQ ID NO: 7) and 5'-GCTCTA-GAGCTCTTCAGTGCATAGGC-3' (SEQ ID NO: 8) thus introducing artificial XbaI and KpnI cutting sites on the ends of the fragment. To decrease the error rate during the PCR amplification Phusion™ high-fidelity PCR Kit (Finnzymes) was used. Subsequently, the fragment was digested with XbaI and KpnI and subcloned into pSK vector digested with the same restriction endonucleases (pSKHLAMB2 plasmid). To verify the integrity of the sequence several clones of pSKHLAMB2 plasmid were sequenced. Sequencing was performed on an ABI PRISM™ 310 Genetic Analyzer (Perkin Elmer) using ABI PRISM® BigDye™ Terminator Cycle Sequencing kit (PE Applied Biosystems). Only complete matches with the NCBI database human laminin β2 sequence were selected for further cloning.

Expression Constructs

For expression of the human laminin β2 chain pSKHLAMB2 plasmid was digested with XbaI and KpnI and subcloned into XbaI-KpnI treated pcDNA 3.1(+) vector (Invitrogen).

The constructs used for expression of human laminin α4 (HA4 construct) and γ1 (HG1 construct) have been described previously (Kortesmaa, J. et al., J. Biol. Chem. 275(20), 14853-9 (2000)).

Antibodies

Anti-laminin β2 (MAB2066) monoclonal antibody (mAb) was purchased from R@D Systems. Anti-laminin α4 mAb was kindly provided by Dr. Patarroyo (Wondimu, Z. Blood 104(6), 1859-66 (2004)). Anti-laminin β1 mAb (MAB1921) was purchased from CHEMICON. Anti-laminin γ1 (H-190) rabbit polyclonal antibody was purchased from SANTA CRUZ Biotechnology, Inc.

Production and Purification of Recombinant Laminin-421 r-laminin-421 was produced in human embryonic kidney cells (HEK293, ATCC CRL-1573) cultured in DMEM, pyruvate, 10% FCS in humidified 5% $CO_2$ atmosphere at 37° C. Wild-type cells were transfected using the standard calcium-phosphate method with the HG1 construct and stable colonies were selected using 100 mg/ml hygromycin (Cayla). All further cell culture and clonal expansion was carried out in continuous presence of relevant selection antibiotics. A highly expressing clone was then transfected with the human laminin β2 construct and stable clones were selected using 500 mg/ml G418 (LIFE TECHNOLOGIES).

A clone highly expressing both laminin γ1 and laminin β2 was finally transfected with the HA4 construct and stable colonies were selected using 200 mg/ml zeocin (Cayla). The clones showing the highest secretion were expanded further.

For production of r-laminin-421, confluent cells were cultured in DMEM supplemented with 1 mM pyruvate and insulin-transferrin-selen supplement (SIGMA) for up to five days. r-laminin-421 was affinity purified using anti-FLAG M2 matrix (SIGMA). The collected medium was incubated in batch mode with the matrix overnight at 4° C. with agitation. Bound r-laminin-421 was competitively eluted with 50 mg/ml FLAG peptide (SIGMA) in TBS/E (50 mM Tris-Cl, pH 7.5, 150 mM NaCl, 1 mM EDTA) at room temperature. The elute was concentrated and the buffer was replaced by PBS using 30 kD cut-off ultrafiltration (MILLIPORE). Finally the concentrated solution was passed through 0.2 mm filter to remove self-aggregated polymers.

Characterization of Recombinant Laminin-421

Secreted laminin in medium and after purification was characterized using 3-8% gradient SDS-PAGE. Proteins were visualized using Sypro staining (BIORAD) or transferred onto PVDF. The membranes were probed with antibodies described above. After washing, the membranes were incubated with HRP-conjugated goat antibodies. The immunoreactivity was detected by a chemiluminescent kit (Life Science Products) according to the manufacturer's instructions.

RESULTS

Production and Characterization of Recombinant Laminin-421

Conditioned medium from wild-type HEK293 cells did not react in western blotting with the anti-laminin α4, anti-laminin β2, anti-laminin γ1, or anti-FLAG Abs, indicating that these cells express endogenous laminins at very low amounts if at all. After triple transfection, the best cell clone produced 2-3 mg of r-laminin-421 per liter of medium, which is quite high considering the size and complexity of the protein.

Immunoaffinity purification with anti-FLAG M2 matrix followed by competitive elution with FLAG-peptide resulted in highly purified protein as seen in silver stained SDS-PAGE gels. Human r-laminin-421 was characterized using SDS-PAGE. An immunoblot of conditioned medium and r-laminin-421 was performed under non reducing and reducing conditions: Proteins on 3-8% gels were transferred onto PVDF membranes followed by staining with antibodies against laminin α4, β2 (MAB2066), β1 (MAB1921) and γ1 (H-19). The control was a medium conditioned by untransfected HEK293 cells stained with antibody against laminin α4. Under reducing conditions, two bands were seen, a 220 kD band corresponding to the laminin α4 chain and a 200 kD band corresponding to the laminin β2 and γ1 chains, which have similar molecular weights. In Western blotting of the conditioned medium under reducing conditions, a band of approximately 220 kDa could be seen with the laminin α4 mAb. Under non-reducing conditions, most of the protein appeared at the top of the gel as a very high molecular weight band, which was immunoreactive with α4, β2 and γ1 antibodies but not β1, showing that the r-laminin-421 was produced as disulfide-crosslinked heterotrimer.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An isolated recombinant laminin-421 produced by a method comprising:
   providing host cells that express recombinant laminin-421, wherein the recombinant laminin-421 comprises:
   a first chain comprising a polypeptide with 100% identity to a polypeptide sequence of SEQ ID NO: 1,
   a second chain comprising a polypeptide with % identity to a polypeptide sequence of SEQ ID NO: 2, and
   a third chain comprising a polypeptide with 100% identity to a polypeptide sequence of SEQ ID NO: 3,
   wherein the first, second, and third chains assemble to form a recombinant trimeric laminin-421 structure;
   growing the host cells in a cell culture medium under conditions to stimulate expression of the recombinant laminin-421 chains;
   passing the cell culture medium through a column, wherein the column contains a compound that binds to the recombinant laminin-421;
   washing the column to remove unbound materials; and
   eluting the bound recombinant laminin-421 from the column.

2. A pharmaceutical composition, comprising: a) the isolated recombinant laminin-421 of claim 1; and b) a pharmaceutically acceptable carrier.

3. An isolated recombinant laminin-421, comprising:
   a first chain comprising a polypeptide with 100% identity to a polypeptide sequence of SEQ ID NO: 1;
   a second chain comprising a polypeptide with 100% identity to a polypeptide sequence of SEQ ID NO: 2; and
   a third chain comprising a polypeptide with 100% identity to a polypeptide sequence of SEQ ID NO: 3;
   wherein the first, second, and third chains assemble to form a recombinant trimeric laminin-421 structure.

4. A pharmaceutical composition comprising: a) the isolated recombinant laminin-421 of claim 3; and b) a pharmaceutically acceptable carrier.

* * * * *

SEQUENCE LISTING

```
<160> NUMBER OF SEQ ID NOS: 8

<210> SEQ ID NO 1
<211> LENGTH: 1823
<212> TYPE: PRT
<213> ORGANISM: Homo sapiens

<400> SEQUENCE: 1

Met Ala Leu Ser Ser Ala Trp Arg Ser Val Leu Pro Leu Trp Leu Leu
1               5                   10                  15

Trp Ser Ala Ala Cys Ser Arg Ala Ala Ser Gly Asp Asp Asn Ala Phe
            20                  25                  30

Pro Phe Asp Ile Glu Gly Ser Ser Ala Val Gly Arg Gln Asp Pro Pro
        35                  40                  45

Glu Thr Ser Glu Pro Arg Val Ala Leu Gly Arg Leu Pro Pro Ala Ala
    50                  55                  60

Glu Lys Cys Asn Ala Gly Phe Phe His Thr Leu Ser Gly Glu Cys Val
65                  70                  75                  80

Pro Cys Asp Cys Asn Gly Asn Ser Asn Glu Cys Leu Asp Gly Ser Gly
                85                  90                  95

Tyr Cys Val His Cys Gln Arg Asn Thr Thr Gly Glu His Cys Glu Lys
            100                 105                 110

Cys Leu Asp Gly Tyr Ile Gly Asp Ser Ile Arg Gly Ala Pro Gln Phe
        115                 120                 125
```

-continued

```
Cys Gln Pro Cys Pro Cys Pro Leu Pro His Leu Ala Asn Phe Ala Glu
    130                 135                 140

Ser Cys Tyr Arg Lys Asn Gly Ala Val Arg Cys Ile Cys Asn Glu Asn
145                 150                 155                 160

Tyr Ala Gly Pro Asn Cys Glu Arg Cys Ala Pro Gly Tyr Tyr Gly Asn
                165                 170                 175

Pro Leu Leu Ile Gly Ser Thr Cys Lys Lys Cys Asp Cys Ser Gly Asn
            180                 185                 190

Ser Asp Pro Asn Leu Ile Phe Glu Asp Cys Asp Glu Val Thr Gly Gln
            195                 200                 205

Cys Arg Asn Cys Leu Arg Asn Thr Thr Gly Phe Lys Cys Glu Arg Cys
    210                 215                 220

Ala Pro Gly Tyr Tyr Gly Asp Ala Arg Ile Ala Lys Asn Cys Ala Val
225                 230                 235                 240

Cys Asn Cys Gly Gly Pro Cys Asp Ser Val Thr Gly Glu Cys Leu
                245                 250                 255

Glu Glu Gly Phe Glu Pro Pro Thr Gly Met Asp Cys Pro Thr Ile Ser
            260                 265                 270

Cys Asp Lys Cys Val Trp Asp Leu Thr Asp Ala Leu Arg Leu Ala Ala
        275                 280                 285

Leu Ser Ile Glu Glu Gly Lys Ser Gly Val Leu Ser Val Ser Ser Gly
    290                 295                 300

Ala Ala His Arg His Val Asn Glu Ile Asn Ala Thr Ile Tyr Leu
305                 310                 315                 320

Leu Lys Thr Lys Leu Ser Glu Arg Glu Asn Gln Tyr Ala Leu Arg Lys
                325                 330                 335

Ile Gln Ile Asn Asn Ala Glu Asn Thr Met Lys Ser Leu Leu Ser Asp
            340                 345                 350

Val Glu Glu Leu Val Glu Lys Glu Asn Gln Ala Ser Arg Lys Gly Gln
        355                 360                 365

Leu Val Gln Lys Glu Ser Met Asp Thr Ile Asn His Ala Ser Gln Leu
    370                 375                 380

Val Glu Gln Ala His Asp Met Arg Asp Lys Ile Gln Glu Ile Asn Asn
385                 390                 395                 400

Lys Met Leu Tyr Tyr Gly Glu His Glu Leu Ser Pro Lys Glu Ile
                405                 410                 415

Ser Glu Lys Leu Val Leu Ala Gln Lys Met Leu Glu Glu Ile Arg Ser
            420                 425                 430

Arg Gln Pro Phe Phe Thr Gln Arg Glu Leu Val Asp Glu Glu Ala Asp
        435                 440                 445

Glu Ala Tyr Glu Leu Leu Ser Gln Ala Glu Ser Trp Gln Arg Leu His
    450                 455                 460

Asn Glu Thr Arg Thr Leu Phe Pro Val Val Leu Glu Gln Leu Asp Asp
465                 470                 475                 480

Tyr Asn Ala Lys Leu Ser Asp Leu Gln Glu Ala Leu Asp Gln Ala Leu
                485                 490                 495

Asn Tyr Val Arg Asp Ala Glu Asp Met Asn Arg Ala Thr Ala Ala Arg
            500                 505                 510

Gln Arg Asp His Glu Lys Gln Gln Glu Arg Val Arg Glu Gln Met Glu
        515                 520                 525

Val Val Asn Met Ser Leu Ser Thr Ser Ala Asp Ser Leu Thr Thr Pro
    530                 535                 540

Arg Leu Thr Leu Ser Glu Leu Asp Asp Ile Ile Lys Asn Ala Ser Gly
```

```
                545                 550                 555                 560
        Ile Tyr Ala Glu Ile Asp Gly Ala Lys Ser Glu Leu Gln Val Lys Leu
                        565                 570                 575

Ser Asn Leu Ser Asn Leu Ser His Asp Leu Val Gln Glu Ala Ile Asp
                        580                 585                 590

His Ala Gln Asp Leu Gln Gln Glu Ala Asn Glu Leu Ser Arg Lys Leu
                        595                 600                 605

His Ser Ser Asp Met Asn Gly Leu Val Gln Lys Ala Leu Asp Ala Ser
                        610                 615                 620

Asn Val Tyr Glu Asn Ile Val Asn Tyr Val Ser Glu Ala Asn Glu Thr
        625                 630                 635                 640

Ala Glu Phe Ala Leu Asn Thr Thr Asp Arg Ile Tyr Asp Ala Val Ser
                        645                 650                 655

Gly Ile Asp Thr Gln Ile Ile Tyr His Lys Asp Glu Ser Glu Asn Leu
                        660                 665                 670

Leu Asn Gln Ala Arg Glu Leu Gln Ala Lys Ala Glu Ser Ser Ser Asp
                        675                 680                 685

Glu Ala Val Ala Asp Thr Ser Arg Arg Val Gly Gly Ala Leu Ala Arg
                        690                 695                 700

Lys Ser Ala Leu Lys Thr Arg Leu Ser Asp Ala Val Lys Gln Leu Gln
        705                 710                 715                 720

Ala Ala Glu Arg Gly Asp Ala Gln Gln Arg Leu Gly Gln Ser Arg Leu
                        725                 730                 735

Ile Thr Glu Glu Ala Asn Arg Thr Thr Met Glu Val Gln Gln Ala Thr
                        740                 745                 750

Ala Pro Met Ala Asn Asn Leu Thr Asn Trp Ser Gln Asn Leu Gln His
                        755                 760                 765

Phe Asp Ser Ser Ala Tyr Asn Thr Ala Val Asn Ser Ala Arg Asp Ala
                        770                 775                 780

Val Arg Asn Leu Thr Glu Val Val Pro Gln Leu Leu Asp Gln Leu Arg
        785                 790                 795                 800

Thr Val Glu Gln Lys Arg Pro Ala Ser Asn Val Ser Ala Ser Ile Gln
                        805                 810                 815

Arg Ile Arg Glu Leu Ile Ala Gln Thr Arg Ser Val Ala Ser Lys Ile
                        820                 825                 830

Gln Val Ser Met Met Phe Asp Gly Gln Ser Ala Val Glu Val His Ser
                        835                 840                 845

Arg Thr Ser Met Asp Asp Leu Lys Ala Phe Thr Ser Leu Ser Leu Tyr
                        850                 855                 860

Met Lys Pro Pro Val Lys Arg Pro Glu Leu Thr Glu Thr Ala Asp Gln
        865                 870                 875                 880

Phe Ile Leu Tyr Leu Gly Ser Lys Asn Ala Lys Lys Glu Tyr Met Gly
                        885                 890                 895

Leu Ala Ile Lys Asn Asp Asn Leu Val Tyr Val Tyr Asn Leu Gly Thr
                        900                 905                 910

Lys Asp Val Glu Ile Pro Leu Asp Ser Lys Pro Val Ser Ser Trp Pro
                        915                 920                 925

Ala Tyr Phe Ser Ile Val Lys Ile Glu Arg Val Gly Lys His Gly Lys
                        930                 935                 940

Val Phe Leu Thr Val Pro Ser Leu Ser Ser Thr Ala Glu Glu Lys Phe
        945                 950                 955                 960

Ile Lys Lys Gly Glu Phe Ser Gly Asp Asp Ser Leu Leu Asp Leu Asp
                        965                 970                 975
```

-continued

```
Pro Glu Asp Thr Val Phe Tyr Val Gly Gly Val Pro Ser Asn Phe Lys
            980                 985                 990

Leu Pro Thr Ser Leu Asn Leu Pro  Gly Phe Val Gly Cys  Leu Glu Leu
            995                1000                1005

Ala Thr Leu Asn Asn Asp Val  Ile Ser Leu Tyr Asn  Phe Lys His
           1010                1015                1020

Ile Tyr Asn Met Asp Pro Ser  Thr Ser Val Pro Cys  Ala Arg Asp
           1025                1030                1035

Lys Leu Ala Phe Thr Gln Ser  Arg Ala Ala Ser Tyr  Phe Phe Asp
           1040                1045                1050

Gly Ser  Gly Tyr Ala Val Val  Arg Asp Ile Thr Arg  Arg Gly Lys
           1055                1060                1065

Phe Gly  Gln Val Thr Arg Phe  Asp Ile Glu Val Arg  Thr Pro Ala
           1070                1075                1080

Asp Asn  Gly Leu Ile Leu Leu  Met Val Asn Gly Ser  Met Phe Phe
           1085                1090                1095

Arg Leu  Glu Met Arg Asn Gly  Tyr Leu His Val Phe  Tyr Asp Phe
           1100                1105                1110

Gly Phe  Ser Gly Gly Pro Val  His Leu Glu Asp Thr  Leu Lys Lys
           1115                1120                1125

Ala Gln  Ile Asn Asp Ala Lys  Tyr His Glu Ile Ser  Ile Ile Tyr
           1130                1135                1140

His Asn  Asp Lys Lys Met Ile  Leu Val Val Asp Arg  Arg His Val
           1145                1150                1155

Lys Ser  Met Asp Asn Glu Lys  Met Lys Ile Pro Phe  Thr Asp Ile
           1160                1165                1170

Tyr Ile  Gly Gly Ala Pro Pro  Glu Ile Leu Gln Ser  Arg Ala Leu
           1175                1180                1185

Arg Ala  His Leu Pro Leu Asp  Ile Asn Phe Arg Gly  Cys Met Lys
           1190                1195                1200

Gly Phe  Gln Phe Gln Lys Lys  Asp Phe Asn Leu Leu  Glu Gln Thr
           1205                1210                1215

Glu Thr  Leu Gly Val Gly Tyr  Gly Cys Pro Glu Asp  Ser Leu Ile
           1220                1225                1230

Ser Arg  Arg Ala Tyr Phe Asn  Gly Gln Ser Phe Ile  Ala Ser Ile
           1235                1240                1245

Gln Lys  Ile Ser Phe Phe Asp  Gly Phe Glu Gly Gly  Phe Asn Phe
           1250                1255                1260

Arg Thr  Leu Gln Pro Asn Gly  Leu Leu Phe Tyr Tyr  Ala Ser Gly
           1265                1270                1275

Ser Asp  Val Phe Ser Ile Ser  Leu Asp Asn Gly Thr  Val Ile Met
           1280                1285                1290

Asp Val  Lys Gly Ile Lys Val  Gln Ser Val Asp Lys  Gln Tyr Asn
           1295                1300                1305

Asp Gly  Leu Ser His Phe Val  Ile Ser Ser Val Ser  Pro Thr Arg
           1310                1315                1320

Tyr Glu  Leu Ile Val Asp Lys  Ser Arg Val Gly Ser  Lys Asn Pro
           1325                1330                1335

Thr Lys  Gly Lys Ile Glu Gln  Thr Gln Ala Ser Glu  Lys Lys Phe
           1340                1345                1350

Tyr Phe  Gly Gly Ser Pro Ile  Ser Ala Gln Tyr Ala  Asn Phe Thr
           1355                1360                1365
```

-continued

```
Gly Cys Ile Ser Asn Ala Tyr Phe Thr Arg Val Asp Arg Asp Val
    1370                1375                1380

Glu Val Glu Asp Phe Gln Arg Tyr Thr Glu Lys Val His Thr Ser
1385                1390                1395

Leu Tyr Glu Cys Pro Ile Glu Ser Ser Pro Leu Phe Leu Leu His
1400                1405                1410

Lys Lys Gly Lys Asn Leu Ser Lys Pro Lys Ala Ser Gln Asn Lys
1415                1420                1425

Lys Gly Gly Lys Ser Lys Asp Ala Pro Ser Trp Asp Pro Val Ala
1430                1435                1440

Leu Lys Leu Pro Glu Arg Asn Thr Pro Arg Asn Ser His Cys His
1445                1450                1455

Leu Ser Asn Ser Pro Arg Ala Ile Glu His Ala Tyr Gln Tyr Gly
1460                1465                1470

Gly Thr Ala Asn Ser Arg Gln Glu Phe Glu His Leu Lys Gly Asp
1475                1480                1485

Phe Gly Ala Lys Ser Gln Phe Ser Ile Arg Leu Arg Thr Arg Ser
1490                1495                1500

Ser His Gly Met Ile Phe Tyr Val Ser Asp Gln Glu Glu Asn Asp
1505                1510                1515

Phe Met Thr Leu Phe Leu Ala His Gly Arg Leu Val Tyr Met Phe
1520                1525                1530

Asn Val Gly His Lys Lys Leu Lys Ile Arg Ser Gln Glu Lys Tyr
1535                1540                1545

Asn Asp Gly Leu Trp His Asp Val Ile Phe Ile Arg Glu Arg Ser
1550                1555                1560

Ser Gly Arg Leu Val Ile Asp Gly Leu Arg Val Leu Glu Glu Ser
1565                1570                1575

Leu Pro Pro Thr Glu Ala Thr Trp Lys Ile Lys Gly Pro Ile Tyr
1580                1585                1590

Leu Gly Gly Val Ala Pro Gly Lys Ala Val Lys Asn Val Gln Ile
1595                1600                1605

Asn Ser Ile Tyr Ser Phe Ser Gly Cys Leu Ser Asn Leu Gln Leu
1610                1615                1620

Asn Gly Ala Ser Ile Thr Ser Ala Ser Gln Thr Phe Ser Val Thr
1625                1630                1635

Pro Cys Phe Glu Gly Pro Met Glu Thr Gly Thr Tyr Phe Ser Thr
1640                1645                1650

Glu Gly Gly Tyr Val Val Leu Asp Glu Ser Phe Asn Ile Gly Leu
1655                1660                1665

Lys Phe Glu Ile Ala Phe Glu Val Arg Pro Arg Ser Ser Ser Gly
1670                1675                1680

Thr Leu Val His Gly His Ser Val Asn Gly Glu Tyr Leu Asn Val
1685                1690                1695

His Met Lys Asn Gly Gln Val Ile Val Lys Val Asn Asn Gly Ile
1700                1705                1710

Arg Asp Phe Ser Thr Ser Val Thr Pro Lys Gln Ser Leu Cys Asp
1715                1720                1725

Gly Arg Trp His Arg Ile Thr Val Ile Arg Asp Ser Asn Val Val
1730                1735                1740

Gln Leu Asp Val Asp Ser Glu Val Asn His Val Val Gly Pro Leu
1745                1750                1755

Asn Pro Lys Pro Ile Asp His Arg Glu Pro Val Phe Val Gly Gly
```

```
                1760                1765                1770
Val Pro Glu Ser Leu Leu Thr Pro Arg Leu Ala Pro Ser Lys Pro
    1775                1780                1785

Phe Thr Gly Cys Ile Arg His Phe Val Ile Asp Gly His Pro Val
    1790                1795                1800

Ser Phe Ser Lys Ala Ala Leu Val Ser Gly Ala Val Ser Ile Asn
    1805                1810                1815

Ser Cys Pro Ala Ala
    1820

<210> SEQ ID NO 2
<211> LENGTH: 1798
<212> TYPE: PRT
<213> ORGANISM: Homo sapiens

<400> SEQUENCE: 2

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
                20                  25                  30

Gln Ala Pro Ala Pro Asp Val Pro Gly Cys Ser Arg Gly Ser Cys Tyr
            35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
    210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
    290                 295                 300
```

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
            325                 330                 335

Glu Asp Gly His Ser His Ala Cys Arg Lys Cys Glu Cys His Gly His
        340                 345                 350

Thr His Ser Cys His Phe Asp Met Ala Val Tyr Leu Ala Ser Gly Asn
    355                 360                 365

Val Ser Gly Gly Val Cys Asp Gly Cys Gln His Asn Thr Ala Gly Arg
370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Asp Pro Ala Leu Gly
            420                 425                 430

Leu Val Ser Gly Gln Cys Arg Cys Lys Glu His Val Val Gly Thr Arg
        435                 440                 445

Cys Gln Gln Cys Arg Asp Gly Phe Phe Gly Leu Ser Ile Ser Asp Arg
450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala

-continued

```
               725                 730                 735
Ala Leu Glu Arg Gln Ala Thr Phe Glu Arg Tyr Gln Cys His Glu Glu
               740                 745                 750
Gly Leu Val Pro Ser Lys Thr Pro Ser Glu Ala Cys Ala Pro Leu
               755                 760                 765
Leu Ile Ser Leu Ser Thr Leu Ile Tyr Asn Gly Ala Leu Pro Cys Gln
               770                 775                 780
Cys Asn Pro Gln Gly Ser Leu Ser Ser Glu Cys Asn Pro His Gly Gly
           785                 790                 795                 800
Gln Cys Leu Cys Lys Pro Gly Val Val Gly Arg Arg Cys Asp Leu Cys
               805                 810                 815
Ala Pro Gly Tyr Tyr Gly Phe Gly Pro Thr Gly Cys Gln Ala Cys Gln
               820                 825                 830
Cys Ser His Glu Gly Ala Leu Ser Ser Leu Cys Glu Lys Thr Ser Gly
               835                 840                 845
Gln Cys Leu Cys Arg Thr Gly Ala Phe Gly Leu Arg Cys Asp Arg Cys
           850                 855                 860
Gln Arg Gly Gln Trp Gly Phe Pro Ser Cys Arg Pro Cys Val Cys Asn
865                 870                 875                 880
Gly His Ala Asp Glu Cys Asn Thr His Thr Gly Ala Cys Leu Gly Cys
               885                 890                 895
Arg Asp His Thr Gly Gly Glu His Cys Glu Arg Cys Ile Ala Gly Phe
           900                 905                 910
His Gly Asp Pro Arg Leu Pro Tyr Gly Gly Gln Cys Arg Pro Cys Pro
               915                 920                 925
Cys Pro Glu Gly Pro Gly Ser Gln Arg His Phe Ala Thr Ser Cys His
           930                 935                 940
Gln Asp Glu Tyr Ser Gln Gln Ile Val Cys His Cys Arg Ala Gly Tyr
945                 950                 955                 960
Thr Gly Leu Arg Cys Glu Ala Cys Ala Pro Gly His Phe Gly Asp Pro
               965                 970                 975
Ser Arg Pro Gly Gly Arg Cys Gln Leu Cys Glu Cys Ser Gly Asn Ile
           980                 985                 990
Asp Pro Met Asp Pro Asp Ala Cys Asp Pro His Thr Gly Gln Cys Leu
           995                 1000                1005
Arg Cys Leu His His Thr Glu Gly Pro His Cys Ala His Cys Lys
           1010                1015                1020
Pro Gly Phe His Gly Gln Ala Ala Arg Gln Ser Cys His Arg Cys
           1025                1030                1035
Thr Cys Asn Leu Leu Gly Thr Asn Pro Gln Gln Cys Pro Ser Pro
           1040                1045                1050
Asp Gln Cys His Cys Asp Pro Ser Ser Gly Gln Cys Pro Cys Leu
           1055                1060                1065
Pro Asn Val Gln Gly Pro Ser Cys Asp Arg Cys Ala Pro Asn Phe
           1070                1075                1080
Trp Asn Leu Thr Ser Gly His Gly Cys Gln Pro Cys Ala Cys His
           1085                1090                1095
Pro Ser Arg Ala Arg Gly Pro Thr Cys Asn Glu Phe Thr Gly Gln
           1100                1105                1110
Cys His Cys Arg Ala Gly Phe Gly Gly Arg Thr Cys Ser Glu Cys
           1115                1120                1125
Gln Glu Leu His Trp Gly Asp Pro Gly Leu Gln Cys His Ala Cys
           1130                1135                1140
```

```
Asp Cys Asp Ser Arg Gly Ile Asp Thr Pro Gln Cys His Arg Phe
    1145                1150                1155

Thr Gly His Cys Ser Cys Arg Pro Gly Val Ser Gly Val Arg Cys
    1160                1165                1170

Asp Gln Cys Ala Arg Gly Phe Ser Gly Ile Phe Pro Ala Cys His
    1175                1180                1185

Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
    1235                1240                1245

Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Asp Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530
```

```
Glu Met Val Ala Thr Arg Val Leu Glu Leu Ser Ile Pro Ala Ser
1535                1540                1545

Ala Glu Gln Ile Gln His Leu Ala Gly Ala Ile Ala Glu Arg Val
1550                1555                1560

Arg Ser Leu Ala Asp Val Asp Ala Ile Leu Ala Arg Thr Val Gly
1565                1570                1575

Asp Val Arg Arg Ala Glu Gln Leu Leu Gln Asp Ala Arg Arg Ala
1580                1585                1590

Arg Ser Trp Ala Glu Asp Lys Gln Lys Ala Glu Thr Val Gln
1595                1600                1605

Ala Ala Leu Glu Glu Ala Gln Arg Ala Gln Gly Ile Ala Gln Gly
1610                1615                1620

Ala Ile Arg Gly Ala Val Ala Asp Thr Arg Asp Thr Glu Gln Thr
1625                1630                1635

Leu Tyr Gln Val Gln Glu Arg Met Ala Gly Ala Glu Arg Ala Leu
1640                1645                1650

Ser Ser Ala Gly Glu Arg Ala Arg Gln Leu Asp Ala Leu Leu Glu
1655                1660                1665

Ala Leu Lys Leu Lys Arg Ala Gly Asn Ser Leu Ala Ala Ser Thr
1670                1675                1680

Ala Glu Glu Thr Ala Gly Ser Ala Gln Gly Arg Ala Gln Glu Ala
1685                1690                1695

Glu Gln Leu Leu Arg Gly Pro Leu Gly Asp Gln Tyr Gln Thr Val
1700                1705                1710

Lys Ala Leu Ala Glu Arg Lys Ala Gln Gly Val Leu Ala Ala Gln
1715                1720                1725

Ala Arg Ala Glu Gln Leu Arg Asp Glu Ala Arg Asp Leu Leu Gln
1730                1735                1740

Ala Ala Gln Asp Lys Leu Gln Arg Leu Gln Glu Leu Glu Gly Thr
1745                1750                1755

Tyr Glu Glu Asn Glu Arg Ala Leu Glu Ser Lys Ala Ala Gln Leu
1760                1765                1770

Asp Gly Leu Glu Ala Arg Met Arg Ser Val Leu Gln Ala Ile Asn
1775                1780                1785

Leu Gln Val Gln Ile Tyr Asn Thr Cys Gln
1790                1795

<210> SEQ ID NO 3
<211> LENGTH: 1609
<212> TYPE: PRT
<213> ORGANISM: Homo sapiens

<400> SEQUENCE: 3

Met Arg Gly Ser His Arg Ala Ala Pro Ala Leu Arg Pro Arg Gly Arg
1               5                   10                  15

Leu Trp Pro Val Leu Ala Val Leu Ala Ala Ala Ala Ala Gly Cys
                20                  25                  30

Ala Gln Ala Ala Met Asp Glu Cys Thr Asp Glu Gly Gly Arg Pro Gln
            35                  40                  45

Arg Cys Met Pro Glu Phe Val Asn Ala Ala Phe Asn Val Thr Val Val
        50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95
```

```
Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
            115                 120                 125

Tyr Pro Ser Ser Ile Asn Leu Thr Leu His Leu Gly Lys Ala Phe Asp
        130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
            195                 200                 205

Phe Ser Asp Ile Ser Pro Leu Thr Gly Gly Asn Val Ala Phe Ser Thr
        210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
            275                 280                 285

Asn Gly His Ala Ser Glu Cys Met Lys Asn Glu Phe Asp Lys Leu Val
        290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
            355                 360                 365

Asn Cys Gln Asp Asn Thr Asp Gly Ala His Cys Glu Arg Cys Arg Glu
        370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415

Ser Cys Lys Pro Gly Val Met Gly Asp Lys Cys Asp Arg Cys Gln Pro
            420                 425                 430

Gly Phe His Ser Leu Thr Glu Ala Gly Cys Arg Pro Cys Ser Cys Asp
            435                 440                 445

Pro Ser Gly Ser Ile Asp Glu Cys Asn Ile Glu Thr Gly Arg Cys Val
        450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
                485                 490                 495

Cys Phe Gly His Ser Ser Val Cys Thr Asn Ala Val Gly Tyr Ser Val
            500                 505                 510
```

```
Tyr Ser Ile Ser Ser Thr Phe Gln Ile Asp Glu Asp Gly Trp Arg Ala
            515                 520                 525

Glu Gln Arg Asp Gly Ser Glu Ala Ser Leu Glu Trp Ser Ser Glu Arg
    530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
            580                 585                 590

Glu Asp Leu Val Leu Glu Gly Ala Gly Leu Arg Val Ser Val Pro Leu
        595                 600                 605

Ile Ala Gln Gly Asn Ser Tyr Pro Ser Glu Thr Thr Val Lys Tyr Val
    610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                645                 650                 655

Arg Gly Thr Tyr Ser Glu Arg Ser Ala Gly Tyr Leu Asp Asp Val Thr
            660                 665                 670

Leu Ala Ser Ala Arg Pro Gly Pro Gly Val Pro Ala Thr Trp Val Glu
        675                 680                 685

Ser Cys Thr Cys Pro Val Gly Tyr Gly Gly Gln Phe Cys Glu Met Cys
    690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
                725                 730                 735

Thr Gly Val Cys Asn Cys Arg Asp Asn Thr Ala Gly Pro His Cys Glu
            740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
    770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
                805                 810                 815

Gly Arg Asn Gly Pro Val Arg Leu Cys Arg Leu Cys Gln Cys Ser Asp
            820                 825                 830

Asn Ile Asp Pro Asn Ala Val Gly Asn Cys Asn Arg Leu Thr Gly Glu
        835                 840                 845

Cys Leu Lys Cys Ile Tyr Asn Thr Ala Gly Phe Tyr Cys Asp Arg Cys
    850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
                885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
```

```
                930             935             940
Gly Gln Cys Asp Ile Arg Thr Gly Gln Cys Glu Cys Gln Pro Gly Ile
945                 950             955                 960

Thr Gly Gln His Cys Glu Arg Cys Glu Val Asn His Phe Gly Phe Gly
                965             970             975

Pro Glu Gly Cys Lys Pro Cys Asp Cys His Pro Glu Gly Ser Leu Ser
            980             985             990

Leu Gln Cys Lys Asp Asp Gly Arg Cys Glu Cys Arg Glu Gly Phe Val
        995             1000            1005

Gly Asn Arg Cys Asp Gln Cys Glu Glu Asn Tyr Phe Tyr Asn Arg
    1010            1015            1020

Ser Trp Pro Gly Cys Gln Glu Cys Pro Ala Cys Tyr Arg Leu Val
    1025            1030            1035

Lys Asp Lys Val Ala Asp His Arg Val Lys Leu Gln Glu Leu Glu
    1040            1045            1050

Ser Leu Ile Ala Asn Leu Gly Thr Gly Asp Glu Met Val Thr Asp
    1055            1060            1065

Gln Ala Phe Glu Asp Arg Leu Lys Glu Ala Glu Arg Glu Val Met
    1070            1075            1080

Asp Leu Leu Arg Glu Ala Gln Asp Val Lys Asp Val Asp Gln Asn
    1085            1090            1095

Leu Met Asp Arg Leu Gln Arg Val Asn Asn Thr Leu Ser Ser Gln
    1100            1105            1110

Ile Ser Arg Leu Gln Asn Ile Arg Asn Thr Ile Glu Glu Thr Gly
    1115            1120            1125

Asn Leu Ala Glu Gln Ala Arg Ala His Val Glu Asn Thr Glu Arg
    1130            1135            1140

Leu Ile Glu Ile Ala Ser Arg Glu Leu Glu Lys Ala Lys Val Ala
    1145            1150            1155

Ala Ala Asn Val Ser Val Thr Gln Pro Glu Ser Thr Gly Asp Pro
    1160            1165            1170

Asn Asn Met Thr Leu Leu Ala Glu Glu Ala Arg Lys Leu Ala Glu
    1175            1180            1185

Arg His Lys Gln Glu Ala Asp Asp Ile Val Arg Val Ala Lys Thr
    1190            1195            1200

Ala Asn Asp Thr Ser Thr Glu Ala Tyr Asn Leu Leu Leu Arg Thr
    1205            1210            1215

Leu Ala Gly Glu Asn Gln Thr Ala Phe Glu Ile Glu Glu Leu Asn
    1220            1225            1230

Arg Lys Tyr Glu Gln Ala Lys Asn Ile Ser Gln Asp Leu Glu Lys
    1235            1240            1245

Gln Ala Ala Arg Val His Glu Glu Ala Lys Arg Ala Gly Asp Lys
    1250            1255            1260

Ala Val Glu Ile Tyr Ala Ser Val Ala Gln Leu Ser Pro Leu Asp
    1265            1270            1275

Ser Glu Thr Leu Glu Asn Glu Ala Asn Asn Ile Lys Met Glu Ala
    1280            1285            1290

Glu Asn Leu Glu Gln Leu Ile Asp Gln Lys Leu Lys Asp Tyr Glu
    1295            1300            1305

Asp Leu Arg Glu Asp Met Arg Gly Lys Glu Leu Glu Val Lys Asn
    1310            1315            1320

Leu Leu Glu Lys Gly Lys Thr Glu Gln Gln Thr Ala Asp Gln Leu
    1325            1330            1335
```

Leu Ala Arg Ala Asp Ala Ala Lys Ala Leu Ala Glu Glu Ala Ala
    1340            1345                1350

Lys Lys Gly Arg Asp Thr Leu Gln Glu Ala Asn Asp Ile Leu Asn
1355            1360                1365

Asn Leu Lys Asp Phe Asp Arg Arg Val Asn Asp Asn Lys Thr Ala
1370            1375                1380

Ala Glu Glu Ala Leu Arg Lys Ile Pro Ala Ile Asn Gln Thr Ile
1385            1390                1395

Thr Glu Ala Asn Glu Lys Thr Arg Glu Ala Gln Gln Ala Leu Gly
1400            1405                1410

Ser Ala Ala Asp Ala Thr Glu Ala Lys Asn Lys Ala His Glu
1415            1420                1425

Ala Glu Arg Ile Ala Ser Ala Val Gln Lys Asn Ala Thr Ser Thr
1430            1435                1440

Lys Ala Glu Ala Glu Arg Thr Phe Ala Glu Val Thr Asp Leu Asp
1445            1450                1455

Asn Glu Val Asn Asn Met Leu Lys Gln Leu Gln Glu Ala Glu Lys
1460            1465                1470

Glu Leu Lys Arg Lys Gln Asp Asp Ala Asp Gln Asp Met Met Met
1475            1480                1485

Ala Gly Met Ala Ser Gln Ala Gln Glu Ala Glu Ile Asn Ala
1490            1495                1500

Arg Lys Ala Lys Asn Ser Val Thr Ser Leu Leu Ser Ile Ile Asn
1505            1510                1515

Asp Leu Leu Glu Gln Leu Gly Gln Leu Asp Thr Val Asp Leu Asn
1520            1525                1530

Lys Leu Asn Glu Ile Glu Gly Thr Leu Asn Lys Ala Lys Asp Glu
1535            1540                1545

Met Lys Val Ser Asp Leu Asp Arg Lys Val Ser Asp Leu Glu Asn
1550            1555                1560

Glu Ala Lys Lys Gln Glu Ala Ala Ile Met Asp Tyr Asn Arg Asp
1565            1570                1575

Ile Glu Glu Ile Met Lys Asp Ile Arg Asn Leu Glu Asp Ile Arg
1580            1585                1590

Lys Thr Leu Pro Ser Gly Cys Phe Asn Thr Pro Ser Ile Glu Lys
1595            1600                1605

Pro

<210> SEQ ID NO 4
<211> LENGTH: 7287
<212> TYPE: DNA
<213> ORGANISM: Homo sapiens

<400> SEQUENCE: 4
agcttagagt gggagggcct gggagtagaa ggtaaaaagg gagtggtgag aatgaatgtg      60
agaaggaagc caggacagcg cagtcccag tcccgaacgg ccagggagag gaggtggcct     120
agcgctggcg gggctcaccc caatccgtct gcctttttgat gccgtactct gctggttgcg    180
cagccacctc gggatactgc acacggagag gagggaaaat aagcgaggca ccgccgcacc    240
acgcgggaga cctacggaga cccacagcgc ccgagccctg aagagcact actggatgtc     300 agcggagaaa tggctttgag ctcagcctgg cgctcggttc tgcctctgtg gctcctctgg    360
agcgctgcct gctcccgcgc cgcgtccggg gacgacaacg cttttccttt tgacattgaa    420

```
gggagctcag cggttggcag gcaagacccg cctgagacga gcgaaccccg cgtggctctg    480
ggacgcctgc cgcctgcggc cgagaaatgc aatgctggat tctttcacac cctgtcggga    540
gaatgtgtgc cctgcgactg taatggcaat tccaacgagt gtttggacgg ctcaggatac    600
tgtgtgcact gccagcggaa cacaacagga gagcactgtg aaaagtgtct ggatggttat    660
atcggagatt ccatcagggg agcaccccaa ttctgccagc cgtgcccctg tccctgccc     720 cacttggcca attttgcaga atcctgctat aggaaaaatg gagctgttcg gtgcatttgt    780
aacgaaaatt atgctggacc taactgtgaa agatgtgctc ccggttacta tggaaacccc    840
ttactcattg gaagcacctg taagaaatgt gactgcagtg gaaattcaga tcccaacctg    900
atctttgaag attgtgatga agtcactggc cagtgtagga attgcttacg caacaccacc    960
ggattcaagt gtgaacgttg cgctcctggc tactatgggg acgccaggat agccaagaac   1020
tgtgcagtgt gcaactgcgg gggaggccca tgtgacagta taccggaga atgcttggaa    1080 gaaggttttg aaccccctac aggcatggac tgcccaacca taagctgtga taagtgcgtc   1140
tgggacctga ctgatgcact gcggttagca gcgctctcca tcgaggaagg caaatccggg   1200
gtgctgagcg tatcctctgg ggccgccgct cataggcacg tgaatgaaat caacgccacc   1260
atctacctcc tcaaaacaaa attgtcagaa agagaaaacc aatacgccct aagaaagata   1320
caaatcaaca atgctgagaa cacgatgaaa agccttctgt ctgacgtaga ggaattagtt   1380
gaaaaggaaa atcaagcctc cagaaaagga caacttgttc agaaggaaag catggacacc   1440
attaaccacg caagtcagct ggtagagcaa gcccatgata tgagggataa aatccaagag   1500
atcaacaaca agatgctcta ttatggggaa gagcatgaac ttagccccaa ggaaatctct   1560
gagaagctgg tgttggccca gaagatgctt gaagagatta gaagccgtca accatttttc   1620
acccaacggg agctcgtgga tgaggaggca gatgaggctt acgaactact gagccaggct   1680
gagagctggc agcggctgca caatgagacc cgcactctgt ttcctgtcgt cctggagcag   1740
ctggatgact acaatgctaa gttgtcagat ctccaggaag cacttgacca ggcccttaac   1800
tatgtcaggg atgccgaaga catgaacagg gccacagcag ccaggcagcg ggaccatgag   1860
aaacaacagg aaagagtgag ggaacaaatg gaagtggtga acatgtctct gagcacatct   1920
gcggactctc tgacaacacc tcgtctaact cttttcagaac ttgatgatat aataaagaat   1980
gcgtcaggga tttatgcaga aatagatgga gccaaaagtg aactacaagt aaaactatct   2040
aacctaagta acctcagcca tgatttagtc caagaagcta ttgaccatgc acaggacctt   2100
caacaagaag ctaatgaatt gagcaggaag ttgcacagtt cagatatgaa cgggctggta   2160
cagaaggctt tggatgcatc aaatgtctat gaaaatattg ttaattatgt tagtgaagcc   2220
aatgaaacag cagaatttgc tttgaacacc actgaccgaa tttatgatgc ggtgagtggg   2280
attgatactc aaatcattta ccataaagat gaaagtgaga acctcctcaa tcaagccaga   2340
gaactgcaag caaaggcaga gtctagcagt gatgaagcag tggctgacac tagcaggcgt   2400
gtgggtggag ccctagcaag gaaaagtgcc cttaaaacca gactcagtga tgccgttaag   2460
caactacaag cagcagagag aggggatgcc cagcagcgcc tggggcagtc tagactgatc   2520
accgaggaag ccaacaggac gacgatggag gtgcagcagg ccactgcccc catggccaac   2580
aatctaacca actggtcaca gaatcttcaa cattttgact cttctgctta caacactgca   2640
gtgaactctg ctagggatgc agtaagaaat ctgaccgagg ttgtccctca gctcctggat   2700
cagcttcgta cggttgagca gaagcgacct gcaagcaacg tttctgccag catccagagg   2760
atccgagagc tcattgctca gaccagaagt gttgccagca agatccaagt ctccatgatg   2820
```

-continued

```
tttgatggcc agtcagctgt ggaagtgcac tcgagaacca gtatggatga cttaaaggcc    2880
ttcacgtctc tgagcctgta catgaaaccc cctgtgaagc ggccggaact gaccgagact    2940
gcagatcagt ttatcctgta cctcggaagc aaaaacgcca aaaagagta tgggtctt      3000 gcaatcaaaa atgataatct ggtatacgtc tataatttgg gaactaaaga tgtggagatt    3060
cccctggact ccaagcccgt cagttcctgg cctgcttact tcagcattgt caagattgaa    3120
agggtgggaa acatggaaa ggtgttttta acagtcccga gtctaagtag cacagcagag     3180
gaaaagttca ttaaaaaggg ggaattttcg ggagatgact ctctgctgga cctggaccct    3240
gaggacacag tgttttatgt tggtggagtg ccttccaact tcaagctccc taccagctta    3300
aacctgcctg gctttgttgg ctgcctggaa ctggccactt gaataatga tgtgatcagc     3360 ttgtacaact ttaagcacat ctataatatg accccctcca catcagtgcc atgtgcccga    3420
gataagctgg ccttcactca gagtcgggct gccagttact tcttcgatgg ctccggttat    3480
gccgtggtga gagacatcac aaggagaggg aaatttggtc aggtgactcg ctttgacata    3540
gaagttcgaa caccagctga caacggcctt attctcctga tggtcaatgg aagtatgttt    3600
ttcagactgg aaatgcgcaa tggttaccta catgtgttct atgattttgg attcagcggt    3660
ggccctgtgc atcttgaaga tacgttaaag aaagctcaaa ttaatgatgc aaaataccat    3720
gagatctcaa tcatttacca caatgataag aaaatgatct tggtagttga cagaaggcat    3780
gtcaagagca tggataatga aaagatgaaa ataccttttta cagatatata cattggagga    3840
gctcctccag aaatcttaca atccaggggcc ctcagagcac accttcccct agatatcaac    3900
ttcagaggat gcatgaaggg cttccagttc caaaagaagg acttcaattt actggagcag    3960
acagaaaccc tggagttgg ttatggatgc ccagaagact cacttatatc tcgcagagca     4020
tatttcaatg gacagagctt cattgcttca attcagaaaa tatctttctt tgatggcttt    4080
gaaggaggtt ttaatttccg aacattacaa ccaaatgggt tactattcta ttatgcttca    4140
gggtcagacg tgttctccat ctcactggat aatggtactg tcatcatgga tgtaaaggga    4200
atcaaagttc agtcagtaga taagcagtac aatgatgggc tgtcccactt cgtcattagc    4260
tctgtctcac ccacaagata tgaactgata gtagataaaa gcagagttgg gagtaagaat    4320
cctaccaaag ggaaaataga acagacacaa gcaagtgaaa agaagtttta cttcggtggc    4380
tcaccaatca gtgctcagta tgctaattttc actggctgca taagtaatgc ctactttacc    4440
agggtggata gagatgtgga ggttgaagat ttccaacggt atactgaaaa ggtccacact    4500
tctctttatg agtgtcccat tgagtcttca ccattgtttc tcctccataa aaaggaaaa     4560 aattatccca agcctaaagc aagtcagaat aaaaagggag ggaaaagtaa agatgcacct    4620
tcatgggatc ctgttgctct gaaactccca gagcggaata ctccaagaaa ctctcattgc    4680
caccttttca acagccctag agcaatagag cacgcctatc aatatggagg aacagccaac    4740
agccgccaag agtttgaaca cttaaaagga gattttggtg ccaaatctca gttttccatt    4800
cgtctgagaa ctcgttcctc ccatggcatg atcttctatg tctcagatca agaagagaat    4860
gacttcatga ctctatttttt ggcccatggc cgcttggttt acatgtttaa tgttggtcac    4920
aaaaaactga agattagaag ccaggagaaa tacaatgatg gcctgtggca tgatgtgata    4980
tttattcgag aaaggagcag tggccgactg gtaattgatg gtctccgagt cctagaagaa    5040
agtcttcctc ctactgaagc tacctggaaa atcaagggtc ccatttattt gggaggtgtg    5100
gctcctggaa aggctgtgaa aaatgttcag attaactcca tctacagttt tagtggctgt    5160
```

```
ctcagcaatc tccagctcaa tggggcctcc atcacctctg cttctcagac attcagtgtg    5220 acccttgct ttgaaggccc catggaaaca ggaacttact tttcaacaga aggaggatac      5280
gtggttctag atgaatcttt caatattgga ttgaagtttg aaattgcatt tgaagtccgt    5340
cccagaagca gttccggaac cctggtccac ggccacagtg tcaatgggga gtacctaaat    5400
gttcacatga aaatggaca ggtcatagtg aaagtcaata atggcatcag agattttttcc    5460 acctcagtta cacccaagca gagtctctgt gatggcagat ggcacagaat tacagttatt    5520
agagattcta atgtggttca gttggatgtg gactctgaag tgaaccatgt ggttggaccc    5580
ctgaatccaa aaccaattga tcacagggag cctgtgtttg ttggaggtgt tccagaatct    5640
ctactgacac cacgcttggc ccccagcaaa cccttcacag gctgcatacg ccactttgtg    5700
attgatggac acccagtgag cttcagtaaa gcagccctgg tcagcggcgc cgtaagcatc    5760
aactcctgtc cagcagcctg acatgacaga gcacagctgc ccaaatacaa agttctttag    5820
agcactgaaa gaaacacaaa gccagccagg aggaacagta actcttcctt cgggtggaag    5880
ctttcatcga gttgaacagg acttaaacga atcatcaggg accggatatt tcttatttct    5940
catttggatt cttaaccttg aatccaaagt gtctgcaatg dacaacaatt gaaggagtgg    6000
caaacttact tgtattgaga gcacacgcaa ttcctactgg tgaaattact gtttctgttt    6060
ctaataaaat agaagggatt ccaaataaac acttgcacac atttttgaag tgcggctaga    6120
ttctcagatt caccttttctt ccagggaaga taacttttcaa tctatataaa aatctctgtc   6180
ctaaaactac ctttctttat tttgaagaga cttactaact tacatataat ctaaattaga    6240
tgatagattt gttttttagcc cttttgtttg gtctatcagt ataagaagaa tattttaggt    6300
ttatagctga agttatcaag gtttaataaa gtaaatttct aacagaatac tagaaaaatg    6360
cagtataatt taattttttc taaataagaa acacaggaaa tcaactactt tttcccctttc    6420 cttatctcct taaaagaaaa ataaaattgt acatgagagg aggcttctgt aggttattat     6480
taccattatt gtgtgttcta tgggaatcat tgaggatatc acagcaaaaa cagtaggaca    6540
aaatcataaa attcaattta agagtacaca agtcctttta ttaaaagttt gctcctagcc    6600
tgggcaacat aatgagatcc catctctgca aaaaaatttg tacatgggca tacacctgta    6660
gtcccagcta cttgggaggc tgagacggga ggatcgctta agctcaggag ttcaaggctg    6720
cagtgagcta tgactgctga ctgtacctgc actccagcct gggcaacaga gtgagatcct    6780
gtctcaaaaa caaagtgtgc tctccacata cctgcaacac aactagtctt atttctaaaa    6840
tgttataatc ttttttccaa gtagctacat taatatagtc tagaaaaaaa tggacttgaa    6900
tagctggtag aatattaaaa tatagaaatg aaataaaaga attatatcta aaaacctcaa    6960
ctcagaagac agaaaagag aaaataggcc ctgatatcaa cagaattaac aatacataaa     7020
aggagtaact tttgagggga gaggatataa aatattttga ggaattacca aggggaataa    7080
aacaatgtta ccttgaaatg attatatata tattacatat tggtatatat gtccataccct   7140 acctatatcc cctgctaccc ttctgtctga aatatacaaa taatgataat gttgaagata    7200
tcgataaaca tagctaatgt ctgttcatag aggacttact aagtgccagc caccatgata    7260
agctaaagtt aattatttta tttgttc                                        7287
```

<210> SEQ ID NO 5
<211> LENGTH: 5817
<212> TYPE: DNA
<213> ORGANISM: Homo sapiens

<400> SEQUENCE: 5

-continued

```
gaaggcagtt tccggaggga aggggtaggg ttggggtggg ggcgctctcc gcccggtgtt      60
gcgctccttc ccagaatccg ctccggcctt tccttcctgc cgcgattccc aactttgctc     120
aaagtcgctg gactctaagc tgtcggaggg accgctggac agacctggga actgacagag     180
ggcctggagg gaaacaggcc aaagacccac aggcagagtt gacacggaac cccaaagcaa     240
ggaggagggc tcgggcccga gaccgttcac ctccccttat ccctgttccc ctcttcagga     300
tggagctgac ctcaagggaa agagggaggg gacagcctct gccctgggaa cttcgactgg     360
gcctactgct aagcgtgctg gctgccacac tggcacaggc ccctgccccg gatgtgcctg     420
gctgttccag gggaagctgc tacccccgcca cgggcgacct gctggtgggc cgagctgaca    480
gactgactgc ctcatccact tgtggcctga atggccccca gccctactgc atcgtcagtc     540
acctgcagga cgaaaagaag tgcttccttt gtgactcccg cgcccccttc tctgctagag     600
acaacccaca cagccatcgc atccagaatg tagtcaccag ctttgcacca cagcggcggg     660
cagcctggtg gcagtcagag aatggtatcc ctgcggtcac catccagctg acctggagg      720 ctgagtttca tttcacacac ctcattatga ccttcaagac atttcgccct gctgccatgc     780
tggtggaacg ctcagcagac tttggccgca cctggcatgt gtaccgatat ttctcctatg     840
actgtggggc tgacttccca ggagtcccac tagcacccccc acggcactgg gatgatgtag    900
tctgtgagtc ccgctactca gagattgagc catccactga aggcgaggtc atctatcgtg     960
tgctggaccc tgccatccct atcccagacc cctacagctc acggattcag aacctgttga    1020
agatcaccaa cctacgggtg aacctgactc gtctacacac gttgggagac aacctactcg    1080
acccacggag ggagatccga gagaagtact actatgccct ctatgagctg gttgtacgtg    1140
gcaactgctt ctgctacgga cacgcctcag agtgtgcacc cgccccaggg gcaccagccc    1200
atgctgaggg catggtgcac ggagcttgca tctgcaaaca caacacacgt ggcctcaact    1260
gcgagcagtg tcaggatttc tatcgtgacc tgccctggcg tccggctgag gacggccata    1320
gtcatgcctg taggaagtgt gagtgccatg ggcacaccca cagctgccac ttcgacatgg    1380 ccgtataccct ggcatctggc aatgtgagtg gaggtgtgtg tgatggatgt cagcataaca    1440
cagctgggcg ccactgtgag ctctgtcggc ccttcttcta ccgtgaccca accaaggacc    1500
tgcgggatcc ggctgtgtgc cgctcctgtg attgtgaccc catgggttct caagacggtg    1560
gtcgctgtga ttcccatgat gaccctgcac tgggactggt ctccgccag tgtcgctgca     1620 aagaacatgt ggtgggcact cgctgccagc aatgccgtga tggcttcttt gggctcagca    1680
tcagtgaccc tctgggctgc cggcgatgtc aatgtaatgc acggggcaca gtgcctggga    1740
gcactccttg tgaccccaac agtggatcct gttactgcaa acgtctagtg actggacgtg    1800
gatgtgaccc ctgcctgcct ggccactggg gcctgagcca cgacctgctc ggctgccgcc    1860
cctgtgactg cgacgtgggt ggtgctttgg atccccagtg tgatgagggc acaggtcaat    1920
gccactgccg ccagcacatg gttgggcgac gctgtgagca ggtgcaacct ggctacttcc    1980
ggcccttcct ggaccaccta atttgggagg ctgaggacac ccgagggcag gtgctcgatg    2040
tggtggagcg cctggtgacc cccgggaaaa ctccatcctg gactggctca ggcttcgtgc    2100
ggctacagga aggtcagacc ctggagttcc tggtggcctc tgtgccgaag ctatggact     2160 atgacctgct gctgcgctta gagccccagg tccctgagca atgggcagag ttggaactga    2220
ttgtgcagcg tccagggcct gtgcctgccc acagcctgtg tgggcatttg gtgcccaagg    2280
atgatcgcat ccaagggact ctgcaaccac atgccaggta cttgatattt cctaatcctg    2340
```

```
tctgccttga gcctggtatc tcctacaagc tgcatctgaa gctggtacgg acaggggaa      2400 gtgcccagcc tgagactccc tactctggac ctggcctgct cattgactcg ctggtgctgc    2460
tgccccgtgt cctggtgcta gagatgttta gtgggggtga tgctgctgcc ctggagcgcc    2520
aggccacctt tgaacgctac caatgccatg aggagggtct ggtgcccagc aagacttctc    2580
cctctgaggc ctgcgcaccc ctcctcatca gcctgtccac cctcatctac aatggtgccc    2640
tgccatgtca gtgcaaccct caaggttcac tgagttctga gtgcaaccct catggtggtc    2700
agtgcctgtg caagcctgga gtggttgggc gccgctgtga cctctgtgcc cctggctact    2760
atggctttgg ccccacaggc tgtcaagcct gccagtgcag ccacgagggg gcactcagca    2820
gtctctgtga aaagaccagt gggcaatgtc tctgtcgaac tggtgccttt gggcttcgct    2880
gtgaccgctg ccagcgtggc cagtggggat ccctagctg ccggccatgt gtctgcaatg     2940
ggcatgcaga tgagtgcaac acccacacag gcgcttgcct gggctgccgt gatcacacag    3000
ggggtgagca ctgtgaaagg tgcattgctg gtttccacgg ggaccacgg ctgccatatg     3060 ggggccagtg ccggccctgt ccctgtcctg aaggccctgg gagccaacgg cactttgcta    3120
cttcttgcca ccaggatgaa tattcccagc agattgtgtg ccactgccgg gcaggctata    3180
cggggctgcg atgtgaagct tgtgcccctg gcactttggg ggacccatca aggccaggtg    3240
gccggtgcca actgtgtgag tgcagtggga acattgaccc aatggatcct gatgcctgtg    3300
acccccacac ggggcaatgc ctgcgctgtt tacaccacac agagggtcca cactgtgccc    3360
actgcaagcc tggcttccat gggcaggctg cccgacagag ctgtcaccgc tgcacatgca    3420
acctgctggg cacaaatccg cagcagtgcc catctcctga ccagtgccac tgtgatccaa    3480
gcagtgggca gtgcccatgc ctccccaatg tccagggccc tagctgtgac cgctgtgccc    3540
ccaacttctg gaacctcacc agtggccatg gttgccagcc ttgtgcctgc cacccaagcc    3600
gggccagagg ccccacctgc aacgagttca gggcagtg ccactgccgt gccggctttg     3660
gagggcggac ttgttctgag tgccaagagc tccactgggg agaccctggg ttgcagtgcc    3720
atgcctgtga ttgtgactct cgtggaatag atacacctca gtgtcaccgc ttcacaggtc    3780
actgcagctg ccgcccaggg gtgtctggtg tgcgctgtga ccagtgtgcc cgtggcttct    3840
caggaatctt tcctgcctgc catccctgcc atgcatgctt cggggattgg gaccgagtgg    3900
tgcaggactt ggcagcccgt acacagcgcc tagagcagcg ggcgcaggag ttgcaacaga    3960
cgggtgtgct gggtgccttt gagagcagct tctggcacat gcaggagaag ctgggcattg    4020
tgcagggcat cgtaggtgcc cgcaacacct cagccgcctc cactgcacag cttgtggagg    4080
ccacagagga gctgcggcgt gaaattgggg aggccactga gcacctgact cagctcgagg    4140
cagacctgac agatgtgcaa gatgagaact caatgccaa ccatgcacta agtggtctgg     4200
agcgagatag gcttgcactt aatctcacac tgcggcagct cgaccagcat cttgacttgc    4260
tcaaacattc aaacttcctg ggtgcctatg acagcatccg gcatgcccat agccagtctg    4320
cagaggcaga acgtcgtgcc aatacctcag ccctggcagt acctagccct gtgagcaact    4380
cggcaagtgc tcggcatcgg acagaggcac tgatggatgc tcagaaggag gacttcaaca    4440
gcaaacacat ggccaaccag cgggcacttg caagctctc tgcccatacc cacaccctga     4500
gcctgacaga cataaatgag ctggtgtgtg ggcaccagg ggatgcaccc tgtgctacaa     4560
gcccttgtgg gggtgccggc tgtcgagatg aggatgggca ccgcgctgt ggggcctca     4620 gctgcaatgg ggcagcggct acagcagacc tagcactggg ccgggcccgg cacacacagg    4680
cagagctgca gcgggcactg gcagaaggtg gtagcatcct cagcagagtg gctgagactc    4740
```

```
gtcggcaggc aagcgaggca cagcagcggg cccaggcagc cctggacaag gctaatgctt    4800
ccaggggaca ggtggaacag gccaaccagg aacttcaaga acttatccag agtgtgaagg    4860
acttcctcaa ccaggagggg gctgatcctg atagcattga aatggtggcc acacgggtgc    4920
tagagctctc catcccagct tcagctgagc agatccagcc cctggcgggt gcgattgcag    4980
agcgagtccg gagcctggca gatgtggatg cgatcctggc acgtactgta ggagatgtgc    5040
gtcgtgccga gcagctactg caggatgcac ggcgggcaag gagctgggct gaggatgaga    5100
aacagaaggc agagacagta caggcagcac tggaggaggc ccagcgggca cagggtattg    5160
cccagggtgc catccggggg gcagtggctg acacacggga cacagagcag accctgtacc    5220
aggtacagga aggatggca ggtgcagagc gggcactgag ctctgcaggt gaaagggctc    5280
```

```
gcctgaacac ttttggagat gaagtgttta acgatcccaa agttctcaag tcctattatt    1080
atgccatctc tgattttgct gtaggtggca gatgtaaatg taatggacac gcaagcgagt    1140
gtatgaagaa cgaatttgat aagctggtgt gtaattgcaa acataacaca tatggagtag    1200
actgtgaaaa gtgtcttcct ttcttcaatg accggccgtg gaggagggca actgcggaaa    1260
gtgccagtga atgcctgccc tgtgattgca atggtcgatc ccaggaatgc tacttcgacc    1320
ctgaactcta tcgttccact ggccatgggg ccactgtac caactgccag ataacacag     1380 atggcgccca ctgtgagagg tgccgagaga acttcttccg ccttggcaac aatgaagcct    1440
gctcttcatg ccactgtagt cctgtgggct ctctaagcac acagtgtgat agttacggca    1500
gatgcagctg taagccagga gtgatggggg acaaatgtga ccgttgccag cctggattcc    1560
attctctcac tgaagcagga tgcaggccat gctcttgtga tccctctggc agcatagatg    1620
aatgtaatat tgaaacagga agatgtgttt gcaaagacaa tgtcgaaggc ttcaattgtg    1680
aaagatgcaa acctggattt tttaatctgg aatcatctaa tcctcggggt tgcacaccct    1740
gcttctgctt tgggcattct tctgtctgta caaacgctgt tggctacagt gtttattcta    1800
tctcctctac ctttcagatt gatgaggatg gtggcgtgc ggaacagaga gatggctctg     1860
aagcatctct cgagtggtcc tctgagaggc aagatatcgc cgtgatctca gacagctact    1920
ttcctcggta cttcattgct cctgcaaagt tcttgggcaa gcaggtgttg agttatggtc    1980
agaacctctc cttctccttt cgagtggaca ggcgagatac tcgcctctct gcagaagacc    2040
ttgtgcttga gggagctggc ttaagagtat ctgtacccct tgatcgctcag ggcaattcct    2100 atccaagtga gaccactgtg aagtatgtct tcaggctcca tgaagcaaca gattacccctt    2160 ggaggcctgc tcttaccccct tttgaatttc agaagctcct aaacaacttg acctctatca    2220
agatacgtgg gacatacagt gagagaagtg ctggatattt ggatgatgtc accctggcaa    2280
gtgctcgtcc tgggcctgga gtccctgcaa cttgggtgga gtcctgcacc tgtcctgtgg    2340
gatatggagg gcagttttgt gagatgtgcc tctcaggtta cagaagagaa actcctaatc    2400
ttggaccata cagtccatgt gtgctttgcg cctgcaatgg acacagcgag acctgtgatc    2460
ctgagacagg tgtttgtaac tgcagagaca atacggctgg cccgcactgt gagaagtgca    2520
gtgatgggta ctatggagat tcaactgcag gcacctcctc cgattgccaa ccctgtccgt    2580
gtcctggagg ttcaagttgt gctgttgttc caagacaaa ggaggtggtg tgcaccaact    2640
gtcctactgg caccactggt aagagatgtg agctctgtga tgatggctac tttgagacc    2700 ccctgggtag aaaacggccct gtgagacttt gccgcctgtg ccagtgcagt gacaacatcg    2760
atcccaatgc agttggaaat tgcaatcgct tgacgggaga atgcctgaag tgcatctata    2820
acactgctgg cttctattgt gaccggtgca aagacggatt ttttggaaat ccctggctc    2880 ccaatccagc agacaaatgc aaagcctgca attgcaatct gtatgggacc atgaagcagc    2940
agagcagctg taaccccgtg acggggcagt gtgaatgttt gcctcacgtg actggccagg    3000
actgtggtgc ttgtgaccct ggattctaca atctgcagag tgggcaaggc tgtgagaggt    3060
gtgactgcca tgccttgggc tccaccaatg gcagtgtga catccgcacc ggccagtgtg    3120
agtgccagcc cggcatcact ggtcagcact gtgagcgctg tgaggtcaac cactttgggt    3180
ttggacctga aggctgcaaa ccctgtgact gtcatcctga gggatctctt tcacttcagt    3240
gcaaagatga tggtcgctgt gaatgcagag aaggctttgt gggaaatcgc tgtgaccagt    3300
gtgaagaaaa ctatttctac aatcggtctt ggcctggctg ccaggaatgt ccagcttgtt    3360
accggctggt aaaggataag gttgctgatc atagagtgaa gctccaggaa ttagagagtc    3420
```

```
tcatagcaaa ccttggaact ggggatgaga tggtgacaga tcaagccttc gaggatagac    3480
taaaggaagc agagagggaa gttatggacc tccttcgtga ggcccaggat gtcaaagatg    3540
ttgaccagaa tttgatggat cgcctacaga gagtgaataa cactctgtcc agccaaatta    3600
gccgtttaca gaatatccgg aataccattg aagagactgg aaacttggct gaacaagcgc    3660
gtgcccatgt agagaacaca gagcggttga ttgaaatcgc atccagagaa cttgagaaag    3720
caaaagtcgc tgctgccaat gtgtcagtca ctcagccaga atctacaggg gacccaaaca    3780
acatgactct tttggcagaa gaggctcgaa agcttgctga acgtcataaa caggaagctg    3840
atgacattgt tcgagtggca aagacagcca atgatacgtc aactgaggca tacaacctgc    3900
ttctgaggac actggcagga gaaaatcaaa cagcatttga gattgaagag cttaatagga    3960
agtatgaaca agcgaagaac atctcacagg atctggaaaa acaagctgcc cgagtacatg    4020
aggaggccaa aagggccggt gacaaagctg tggagatcta tgccagcgtg gctcagctga    4080
gcccttttgga ctctgagaca ctggagaatg aagcaaataa cataaagatg gaagctgaga    4140
atctggaaca actgattgac cagaaattaa agattatga ggacctcaga gaagatatga    4200
gagggaagga acttgaagtc aagaaccttc tggagaaagg caagactgaa cagcagaccg    4260
cagaccaact cctagcccga gctgatgctg ccaaggccct cgctgaagaa gctgcaaaga    4320
agggacggga taccttacaa gaagctaatg acattctcaa caacctgaaa gattttgata    4380
ggcgtgtgaa cgataacaag acggccgcag aggaggcact aaggaagatt cctgccatca    4440
accagaccat cactgaagcc aatgaaaaga ccagagaagc ccagcaggcc ctgggcagtg    4500
ctgcggcgga tgccacagag gccaagaaca aggcccatga ggcggagagg atcgcgagcg    4560
ctgtccaaaa gaatgccacc agcaccaagg cagaagctga agaactttt gcagaagtta    4620
cagatctgga taatgaggtg aacaatatgt tgaagcaact gcaggaagca gaaaaagagc    4680
taaagagaaa acaagatgac gctgaccagg acatgatgat ggcagggatg gcttcacagg    4740
ctgctcaaga agccgagatc aatgccagaa aagccaaaaa ctctgttact agcctcctca    4800
gcattattaa tgacctcttg gagcagctgg ggcagctgga tacagtggac ctgaataagc    4860
taaacgagat tgaaggcacc ctaaacaaag ccaaagatga aatgaaggtc agcgatcttg    4920
ataggaaagt gtctgacctg gagaatgaag ccaagaagca ggaggctgcc atcatggact    4980
ataaccgaga tatcgaggag atcatgaagg acattcgcaa tctggaggac atcaggaaga    5040
ccttaccatc tggctgcttc aacaccccgt ccattgaaaa gccctagtgt ctttagggct    5100
ggaaggcagc atccctctga cagggggggca gttgtgaggc cacagagtgc cttgacacaa    5160
agattacatt tttcagaccc ccactcctct gctgctgtcc atgactgtcc ttttgaacca    5220
ggaaaagtca cagagtttaa agagaagcaa attaaacatc ctgaatcggg aacaaagggt    5280
tttatctaat aaagtgtctc ttccattcac gttgctacct tacccacact ttcccttctg    5340
atttgcgtga ggacgtggca tcctacgtta ctgtacagtg gcataagcac atcgtgtgag    5400
cccatgtatg ctggggtaga gcaagtagcc ctcccctgtc tcatcgatac cagcagaacc    5460
tcctcagtct cagtactctt gtttctatga aggaaaagtt tggctactaa cagtagcatt    5520
gtgatggcca gtatatccag tccatggata aagaaaatgc atctgcatct cctacccctc    5580
ttccttctaa gcaaaaggaa ataaacatcc tgtgccaaag gtattggtca tttagaatgt    5640
cggtagccat ccatcagtgc ttttagttat tatgagtgta ggacactgag ccatccgtgg    5700
gtcaggatgc aattatttat aaaagtctcc aggtgaacat ggctgaagat ttttctagta    5760
```

```
tattaataat tgactaggaa gatgaacttt ttttcagatc tttgggcagc tgataattta   5820
aatctggatg ggcagcttgc actcaccaat agaccaaaag acatcttttg atattcttat   5880
aaatggaact tacacagaag aaatagggat atgataacca ctaaaatttt gttttcaaaa   5940
tcaaactaat tcttacagct tttttattag ttagtcttgg aactagtgtt aagtatctgg   6000
cagagaacag ttaatcccta aggtcttgac aaaacagaag aaaaacaagc ctcctcgtcc   6060
tagtcttttc tagcaaaggg ataaaactta gatggcagct tgtactgtca gaatcccgtg   6120
tatccatttg ttcttctgtt ggagagatga gacatttgac ccttagctcc agttttcttc   6180
tgatgtttcc atcttccaga atccctcaaa aacattgtt tgccaaatcc tggtggcaaa    6240
tacttgcact cagtatttca cacagctgcc aacgctatcg agttcctgca ctttgtgatt   6300
taaatccact ctaaaccttc cctctaagtg tagagggaag acccttacgt ggagtttcct   6360
agtgggcttc tcaacttttg atcctcagct ctgtggtttt aagaccacag tgtgacagtt   6420
ccctgccaca caccccttc ctcctaccaa cccacctttg agattcatat atagccttta    6480
acactatgca actttgtact tgcgtagca ggggcggggt gggggaaag aaactattat     6540 ctgacacact ggtgctatta attatttcaa atttatattt ttgtgtgaat gttttgtgtt   6600
ttgtttatca tgattataga ataaggaatt tatgtaaata tacttagtcc tatttctaga   6660 atgcacactct gttcactttg ctcaatttt cctcttcact ggcacaatgt atctgaatac    6720
ctccttccct cccttctaga attctttgga ttgtactcca aagaattgtg ccttgtgttt   6780
gcagcatctc cattctctaa aattaatata attgctttcc tccacaccca gccactgtaa   6840
agaggtaact tgggtcctct tccattgcag tcctgatgat cctaacctgc agcacggtgg   6900
ttttacaatg ttccagagca ggaacgccag gttgacaagc tatggtagga ttaggaaagt   6960
ttgctgaaga ggatctttga cgccacagtg ggactagcca ggaatgaggg agaaatgccc   7020
tttctggcaa ttgttggagc tggataggta agttttataa gggagtacat tttgactgag   7080
cacttagggc atcaggaaca gtgctactta ctgatgggta gactgggaga ggtggtgtaa   7140
cttagttctt gatgatccca cttcctgttt ccatctgctt gggatatacc agagtttacc   7200
acaagtgttt tgacgatata ctcctgagct ttcactctgc tgcttctccc aggcctcttc   7260
tactatggca ggagatgtgg cgtgctgttg caaagttttc acgtcattgt tcctggcta    7320 gttcatttca ttaagtggct acatcctaac atatgcattt ggtcaaggtt gcagaagagg   7380
actgaagatt gactgccaag ctagtttggg tgaagttcac tccagcaagt ctcaggccac   7440
aatggggtgg tttggtttgg tttccttta actttctttt tgttatttgc ttttctcctc   7500
cacctgtgtg gtatattttt taagcagaat tttattttt aaaataaaag gttctttaca   7560
agatgatacc ttaattacac tcccgcaaca cagccattat tttattgtct agctccagtt   7620 atctgtatttt tatgtaatgt aattgacagg atggctgctg cagaatgctg gttgacacag   7680
ggattattat actgctattt ttccctgaat ttttttcctt tgaattccaa ctgtggacct   7740
tttatatgtg ccttcacttt agctgtttgc cttaatctct acagccttgc tctccggggt   7800
ggttaataaa atgcaacact tggcattttt atgttttaag aaaaacagta ttttatttat   7860
aataaaatct gaatatttgt aacccttta                                    7889
```

<210> SEQ ID NO 7
<211> LENGTH: 24
<212> TYPE: DNA
<213> ORGANISM: Artificial Sequence
<220> FEATURE:
<223> OTHER INFORMATION: DNA primer sequence

```
<400> SEQUENCE: 7
gtggtaccca caggcagagt tgac                                              24

<210> SEQ ID NO 8
<211> LENGTH: 26
<212> TYPE: DNA
<213> ORGANISM: Artificial Sequence
<220> FEATURE:
<223> OTHER INFORMATION: DNA primer sequence

<400> SEQUENCE: 8
gctctagagc tcttcagtgc ataggc                                            26
```